(12) United States Patent
Björck et al.

(10) Patent No.: US 6,833,355 B1
(45) Date of Patent: Dec. 21, 2004

(54) USE OF PROTEIN H AS CYTOSTATIC AGENT

(75) Inventors: Lars H. Björck, Lund (SE); Inga-Maria Frick, Staffanstorp (SE); Tomas Borje Leandersson, Staffanstorp (SE); Eugen Jan Karol Axcrona, Lund (SE)

(73) Assignee: Hansa Medical AB, Lund (SE)

( * ) Notice: Subject to any disclaimer, the term of this patent is extended or adjusted under 35 U.S.C. 154(b) by 0 days.

(21) Appl. No.: 09/569,348

(22) Filed: May 11, 2000

Related U.S. Application Data

(63) Continuation of application No. PCT/GB98/03387, filed on Nov. 11, 1998.

(30) Foreign Application Priority Data

Nov. 11, 1997 (GB) .............................................. 9723824

(51) Int. Cl.$^7$ ........................ A61K 38/16; C07K 14/195
(52) U.S. Cl. ........................ 514/12; 530/300; 530/350; 530/825
(58) Field of Search ........................... 514/12; 530/300, 530/350, 825

(56) References Cited

FOREIGN PATENT DOCUMENTS

| EP | 371 199 A1 | 6/1990 |
|---|---|---|
| WO | WO 91/19740 | 12/1991 |

OTHER PUBLICATIONS

Burgess et al "Possible Dissociation of the Heparin–binding and Mitogenic Acitivies of Heparin–binding Growth Factor–1 from Its Receptor–binding Activities by Site–directed Mutagenesis of a single Lysine Residue", Journal of Cellular Biology, 1990, vol. 1.*
Lazar et al, "Transforming Growth Factor Alpha: Mutation of Aspartic Acid 47 and Leuine 48 Results in Different Biological Activities", Molecular and Cellular Biology, 1988, vol. 8, pp. 1247–1252.*
Genbank Accession No:NP_047206, haemagglutinin protein H.*
Ciaiolo et al, "Enhancement of methotrexate cytotoxicity by modulation of proliferative activity in normal and neoplastic T lymphocytes and in a myeloid leukemia cell line", Tumori, 1988, vol. 74, pp. 537–542.*
Hultsch et al, "The effect of immunophilin ligands rapamycin and FK506 on the proliferation of mast cells and other hemaopoietic cell lines", Molecular Biology of the Cell, 1992, vol. 3, pp. 981–987.*
Balkwill, FR, "Tumor necrosis factor", British Medical Bulletin, 1989, vol. 45, pp. 389–400.*
Reiger et al, Glossary of Genetics and Cytogenetics, 4th edition, 1976, pp. 17–18.*
Mathews and Van Holde, Biochemistry (textbook), 2nd edition, 1996, pp. 165–171.*
Matthews, B., "Genetic and structural analysis of the protein stability problem", in Perspectives in Biochemistry, Hans Neurath, Ed., 1989, vol. 1, pp. 6–9.*
Axcrona et al., "Multiple Ligand Interactions for Bacterial Immunoglobulin–Binding Proteins on Human and Murine Cells of the Hematopoetic Lineage," *Scandinavian Journal of Immunology* 42(3):359–367, 1995.
Frick et al., "Protein H—a surface protein of *Streptococcus pyogenes* with separate binding sites for IgG and albumin," *Molecular Microbiology* 12(1): 143–151, 1994.
Identification and Characterization of SET, a Nuclear Phosphoprotein Encoded by the Translocation Break Point in Acute Undifferentiated Leukemia: Authors(s) Yoshifumi Adachi et al., The Journal of Biological Chemistry, (Jan. 1994), vol. 269, No. 3 pages, 2256–2262.
HnRNP Proteins and the Biogenesis of mRNA: Authors (s) Gideon Dreyfuss et al., Annu. Rev. Biochem (1990); vol. 62, pp. 289–321.
Major Nucleolar Proteins Shuttle between Nucleus and Cytoplasm: Authors(s) R.A. Borer et al, Cell, (Feb. 10, 1989) vol. 56, pp. 379–390.

* cited by examiner

Primary Examiner—Karen A. Canella
(74) Attorney, Agent, or Firm—Kalow & Springut LLP

(57) ABSTRACT

The use of protein H, and fragments or derivatives thereof, as cytostatic agents, especially in the treatment of diseases involving undesired cell proliferation.

6 Claims, 7 Drawing Sheets

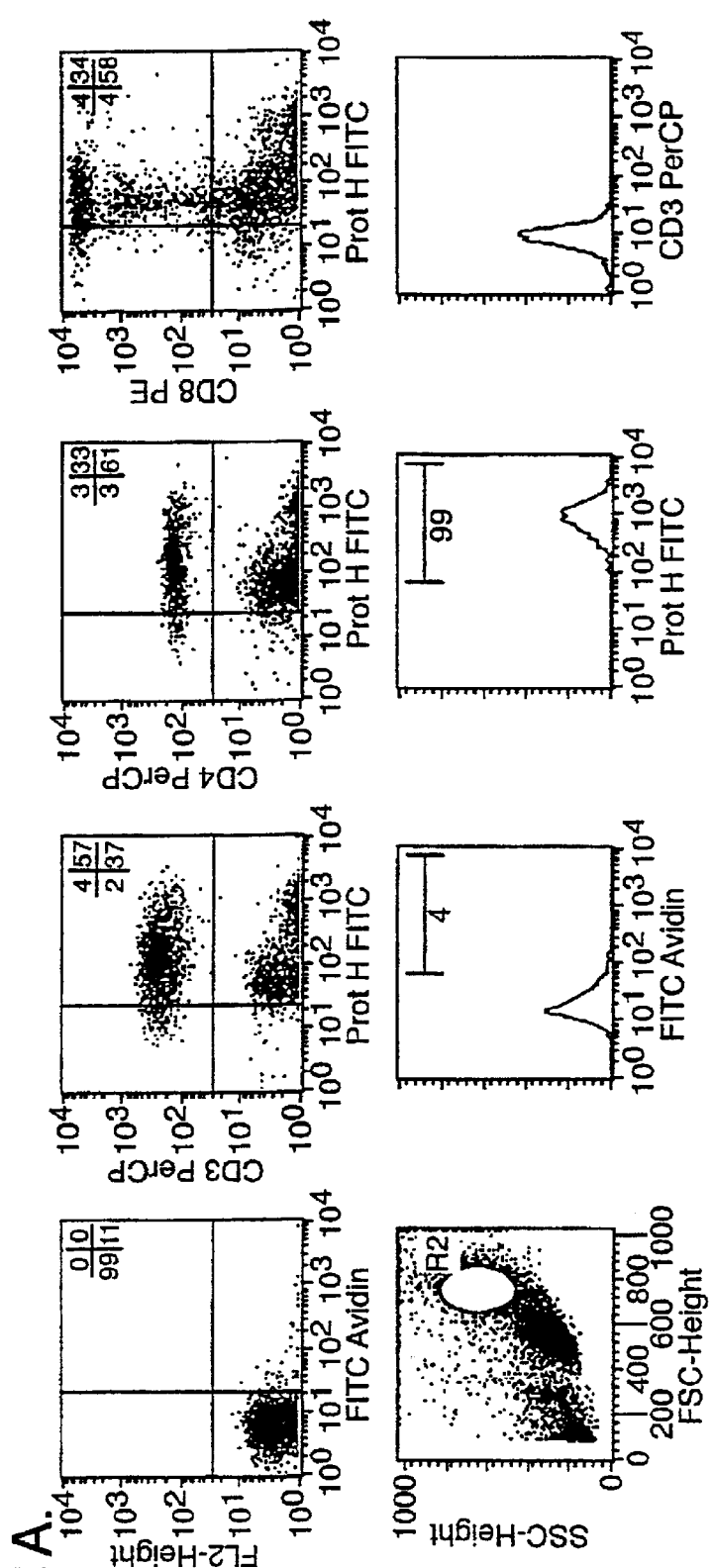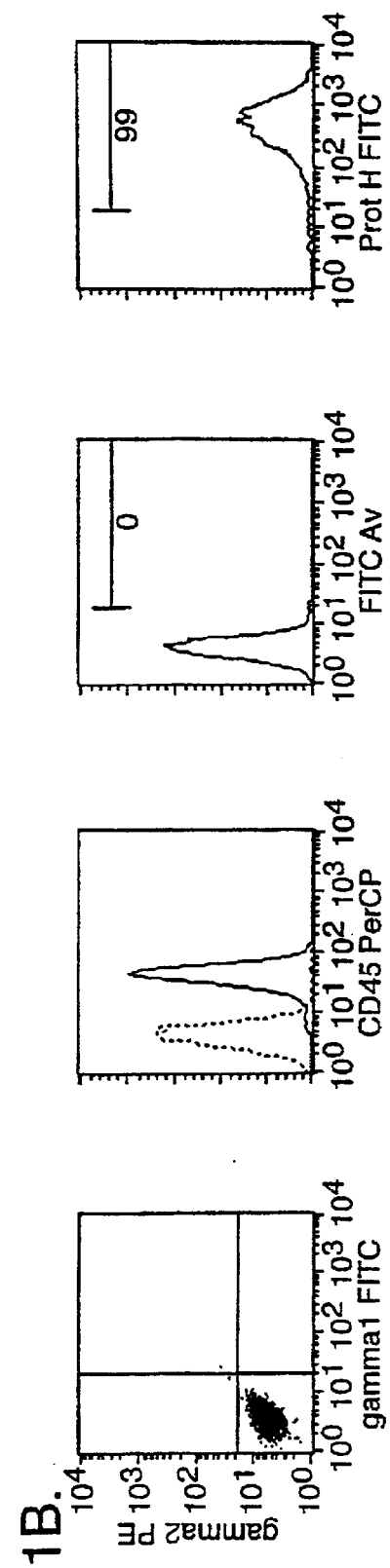
Fig. 1A.
Fig. 1B.

SEQUENCE LISTING

<160> NUMBER OF SEQ ID NOS: 19

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
gcagggcgcc atggaagatt cgatggacat            30

<210> SEQ ID NO 2
<211> LENGTH: 35
<212> TYPE: DNA
<213> ORGANISM: Artificial Sequence
<220> FEATURE:

```
<223> OTHER INFORMATION: PCR primer

<400> SEQUENCE: 2
caggaattct tattaaagag acttcctcca ctgcc                                35

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
caggaattct tattagctac cacctccagg g                                    31

<210> SEQ ID NO 4
<211> LENGTH: 37
<212> TYPE: DNA
<213> ORGANISM: Artificial Sequence
<220> FEATURE:
<223> OTHER INFORMATION: PCR primer

<400> SEQUENCE: 4
ttgatgaagg ttccacagaa aaaagtaaaa cttgctg                              37

<210> SEQ ID NO 5
<211> LENGTH: 1128
<212> TYPE: DNA
<213> ORGANISM: Streptococcus pyogenes
<220> FEATURE:
<221> NAME/KEY: CDS
<222> LOCATION: (1)...(1128)

<400> SEQUENCE: 5
```

| | | | | | | | | | | | | | | | | |
|---|---|---|---|---|---|---|---|---|---|---|---|---|---|---|---|---|
| atg | act | aga | caa | caa | acc | aag | aaa | aat | tat | tca | cta | cgg | aaa | cta | aaa | 48 |
| Met | Thr | Arg | Gln | Gln | Thr | Lys | Lys | Asn | Tyr | Ser | Leu | Arg | Lys | Leu | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | ggt | acg | gct | tca | gta | gcc | gtt | gct | ttg | acc | gtt | ttg | ggc | gca | ggt | 96 |
| Thr | Gly | Thr | Ala | Ser | Val | Ala | Val | Ala | Leu | Thr | Val | Leu | Gly | Ala | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| ttt | gca | aac | caa | aca | aca | gtt | aag | gcg | gaa | ggg | gct | aaa | att | gat | tgg | 144 |
| Phe | Ala | Asn | Gln | Thr | Thr | Val | Lys | Ala | Glu | Gly | Ala | Lys | Ile | Asp | Trp | |
| | 35 | | | | | 40 | | | | | 45 | | | | | |

| | | | | | | | | | | | | | | | | |
|---|---|---|---|---|---|---|---|---|---|---|---|---|---|---|---|---|
| caa | gag | gag | tat | aaa | aag | tta | gac | gaa | gat | aat | gct | aaa | ctt | gtt | gag | 192 |
| Gln | Glu | Glu | Tyr | Lys | Lys | Leu | Asp | Glu | Asp | Asn | Ala | Lys | Leu | Val | Glu | |
| 50 | | | | | 55 | | | | | 60 | | | | | | |

| | | | | | | | | | | | | | | | | |
|---|---|---|---|---|---|---|---|---|---|---|---|---|---|---|---|---|
| gtt | gtt | gaa | acc | aca | agt | ttg | gaa | aac | gaa | aaa | ctc | aag | agt | gag | aat | 240 |
| Val | Val | Glu | Thr | Thr | Ser | Leu | Glu | Asn | Glu | Lys | Leu | Lys | Ser | Glu | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | gag | aat | aag | aaa | aat | tta | gac | aaa | ctt | agc | aaa | gaa | aat | caa | gga | 288 |
| Glu | Glu | Asn | Lys | Lys | Asn | Leu | Asp | Lys | Leu | Ser | Lys | Glu | Asn | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | ctc | gaa | aaa | ttg | gag | ctt | gac | tat | ctc | aaa | aaa | tta | gat | cac | gag | 336 |
| Lys | Leu | Glu | Lys | Leu | Glu | Leu | Asp | Tyr | Leu | Lys | Lys | Leu | Asp | His | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| cac | aaa | gag | cac | caa | aaa | gaa | caa | caa | gaa | caa | gaa | cga | caa | aaa | | 384 |
| His | Lys | Glu | His | Gln | Lys | Glu | Gln | Gln | Glu | Gln | Glu | Arg | Gln | Lys | | |
| | 115 | | | | | 120 | | | | | 125 | | | | | |

| | | | | | | | | | | | | | | | | |
|---|---|---|---|---|---|---|---|---|---|---|---|---|---|---|---|---|
| aat | caa | gaa | caa | tta | gaa | cgt | aaa | tac | caa | cga | gaa | gta | gaa | aaa | cgt | 432 |
| Asn | Gln | Glu | Gln | Leu | Glu | Arg | Lys | Tyr | Gln | Arg | Glu | Val | Glu | Lys | Arg | |
| 130 | | | | | 135 | | | | | 140 | | | | | | |

| | | | | | | | | | | | | | | | | |
|---|---|---|---|---|---|---|---|---|---|---|---|---|---|---|---|---|
| tat | caa | gaa | caa | ctc | caa | aaa | caa | caa | caa | tta | gaa | aca | gaa | aag | caa | 480 |
| Tyr | Gln | Glu | Gln | Leu | Gln | Lys | Gln | Gln | Gln | Leu | Glu | Thr | Glu | Lys | Gln | |

-continued

```
                145                 150                 155                 160
atc tca gaa gct agt cgt aag agc cta agc cgt gac ctt gaa gcg tct         528
Ile Ser Glu Ala Ser Arg Lys Ser Leu Ser Arg Asp Leu Glu Ala Ser
                    165                 170                 175 cgt gca gct aaa aaa gac ctt gaa gct gag cac caa aaa ctt gaa gct         576
Arg Ala Ala Lys Lys Asp Leu Glu Ala Glu His Gln Lys Leu Glu Ala
                180                 185                 190 gag cac caa aaa ctt aaa gaa gac aaa caa atc tca gac gca agt cgt         624
Glu His Gln Lys Leu Lys Glu Asp Lys Gln Ile Ser Asp Ala Ser Arg
            195                 200                 205 caa ggc cta agc cgt gac ctt gaa gcg tct cgt gca gct aaa aaa gag         672
Gln Gly Leu Ser Arg Asp Leu Glu Ala Ser Arg Ala Ala Lys Lys Glu
        210                 215                 220 ctt gaa gca aat cac caa aaa ctt gaa gct gag cac caa aaa ctt aaa         720
Leu Glu Ala Asn His Gln Lys Leu Glu Ala Glu His Gln Lys Leu Lys
225                 230                 235                 240 gaa gac aaa caa atc tca gac gca agt cgt caa ggc cta agc cgt gac         768
Glu Asp Lys Gln Ile Ser Asp Ala Ser Arg Gln Gly Leu Ser Arg Asp
                    245                 250                 255 ctt gaa gcg tct cgt gca gct aaa aaa gag ctt gaa gca aat cac caa         816
Leu Glu Ala Ser Arg Ala Ala Lys Lys Glu Leu Glu Ala Asn His Gln
                260                 265                 270 aaa ctt gaa gca gaa gca aaa gca ctc aaa gaa caa tta gcg aaa caa         864
Lys Leu Glu Ala Glu Ala Lys Ala Leu Lys Glu Gln Leu Ala Lys Gln
            275                 280                 285 gct gaa gaa ctt gca aaa cta aga gct gga aaa gca tca gac tca caa         912
Ala Glu Glu Leu Ala Lys Leu Arg Ala Gly Lys Ala Ser Asp Ser Gln
        290                 295                 300 acc cct gat aca aaa cca gga aac aaa gct gtt cca ggt aaa ggt caa         960
Thr Pro Asp Thr Lys Pro Gly Asn Lys Ala Val Pro Gly Lys Gly Gln
305                 310                 315                 320 gca cca caa gca ggt aca aaa cct aac caa aac aaa gca cca atg aag         1008
Ala Pro Gln Ala Gly Thr Lys Pro Asn Gln Asn Lys Ala Pro Met Lys
                    325                 330                 335 gaa act aag aga cag tta cca tca aca ggt gaa aca gct aac cca ttc         1056
Glu Thr Lys Arg Gln Leu Pro Ser Thr Gly Glu Thr Ala Asn Pro Phe
                340                 345                 350 ttc aca gcg gca gcc ctt act gtt atg gca aca gct gga gta gca gca         1104
Phe Thr Ala Ala Ala Leu Thr Val Met Ala Thr Ala Gly Val Ala Ala
            355                 360                 365 gtt gta aaa cgc aaa gaa gaa aac                                         1128
Val Val Lys Arg Lys Glu Glu Asn
        370                 375
```

<210> SEQ ID NO 6
<211> LENGTH: 376
<212> TYPE: PRT
<213> ORGANISM: Streptococcus pyogenes

<400> SEQUENCE: 6

```
Met Thr Arg Gln Gln Thr Lys Lys Asn Tyr Ser Leu Arg Lys Leu Lys
 1               5                  10                  15

Thr Gly Thr Ala Ser Val Ala Val Ala Leu Thr Val Leu Gly Ala Gly
                20                  25                  30

Phe Ala Asn Gln Thr Thr Val Lys Ala Glu Gly Ala Lys Ile Asp Trp
            35                  40                  45

Gln Glu Glu Tyr Lys Lys Leu Asp Glu Asp Asn Ala Lys Leu Val Glu
        50                  55                  60

Val Val Glu Thr Thr Ser Leu Glu Asn Glu Lys Leu Lys Ser Glu Asn
```

-continued

```
                65                   70                   75                   80
    Glu Glu Asn Lys Lys Asn Leu Asp Lys Leu Ser Lys Glu Asn Gln Gly
                    85                   90                   95
    Lys Leu Glu Lys Leu Glu Leu Asp Tyr Leu Lys Lys Leu Asp His Glu
                   100                  105                  110
    His Lys Glu His Gln Lys Glu Gln Gln Glu Gln Glu Arg Gln Lys
                   115                  120                  125
    Asn Gln Glu Gln Leu Glu Arg Lys Tyr Gln Arg Glu Val Glu Lys Arg
        130                  135                  140
    Tyr Gln Glu Gln Leu Gln Lys Gln Gln Leu Glu Thr Glu Lys Gln
    145                  150                  155                  160
    Ile Ser Glu Ala Ser Arg Lys Ser Leu Ser Arg Asp Leu Glu Ala Ser
                    165                  170                  175
    Arg Ala Ala Lys Lys Asp Leu Glu Ala Glu His Gln Lys Leu Glu Ala
                    180                  185                  190
    Glu His Gln Lys Leu Lys Glu Asp Lys Gln Ile Ser Asp Ala Ser Arg
                    195                  200                  205
    Gln Gly Leu Ser Arg Asp Leu Glu Ala Ser Arg Ala Ala Lys Lys Glu
        210                  215                  220
    Leu Glu Ala Asn His Gln Lys Leu Glu Ala Glu His Gln Lys Leu Lys
    225                  230                  235                  240
    Glu Asp Lys Gln Ile Ser Asp Ala Ser Arg Gln Gly Leu Ser Arg Asp
                    245                  250                  255
    Leu Glu Ala Ser Arg Ala Ala Lys Lys Glu Leu Glu Ala Asn His Gln
                    260                  265                  270
    Lys Leu Glu Ala Glu Ala Lys Ala Leu Lys Glu Gln Leu Ala Lys Gln
                    275                  280                  285
    Ala Glu Glu Leu Ala Lys Leu Arg Ala Gly Lys Ala Ser Asp Ser Gln
        290                  295                  300
    Thr Pro Asp Thr Lys Pro Gly Asn Lys Ala Val Pro Gly Lys Gly Gln
    305                  310                  315                  320
    Ala Pro Gln Ala Gly Thr Lys Pro Asn Gln Asn Lys Ala Pro Met Lys
                    325                  330                  335
    Glu Thr Lys Arg Gln Leu Pro Ser Thr Gly Glu Thr Ala Asn Pro Phe
                    340                  345                  350
    Phe Thr Ala Ala Ala Leu Thr Val Met Ala Thr Ala Gly Val Ala Ala
                    355                  360                  365
    Val Val Lys Arg Lys Glu Glu Asn
        370                  375

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
gcaggaattc atggaagatt cgatggacat                                          30

<210> SEQ ID NO 8
<211> LENGTH: 30
<212> TYPE: DNA
<213> ORGANISM: Artificial Sequence
<220> FEATURE:
<223> OTHER INFORMATION: PCR primer
```

```
<400> SEQUENCE: 8
atagcggccg cttattaaag agacttcctc                             30

<210> SEQ ID NO 9
<211> LENGTH: 18
<212> TYPE: PRT
<213> ORGANISM: Homo sapiens

<400> SEQUENCE: 9

Asp Tyr His Phe Lys Val Asp Asn Asp Glu Asn Glu His Gln Leu Ser
 1               5                  10                  15

Leu Arg

<210> SEQ ID NO 10
<211> LENGTH: 18
<212> TYPE: PRT
<213> ORGANISM: Homo sapiens
<220> FEATURE:
<221> NAME/KEY: VARIANT
<222> LOCATION: 16
<223> OTHER INFORMATION: Xaa = Any Amino Acid

<400> SEQUENCE: 10

Ser Pro Leu Arg Gln Asn Tyr Leu Phe Gly Cys Glu Glu Lys Ala Xaa
 1               5                  10                  15

Lys Asp

<210> SEQ ID NO 11
<211> LENGTH: 18
<212> TYPE: PRT
<213> ORGANISM: Homo sapiens

<400> SEQUENCE: 11

Ser Pro Leu Arg Gln Asn Tyr Leu Phe Gly Cys Glu Leu Lys Ala Asp
 1               5                  10                  15

Lys Asp

<210> SEQ ID NO 12
<211> LENGTH: 8
<212> TYPE: PRT
<213> ORGANISM: Homo sapiens

<400> SEQUENCE: 12

Leu Arg Gln Pro Phe Phe Gln Lys
 1               5

<210> SEQ ID NO 13
<211> LENGTH: 10
<212> TYPE: PRT
<213> ORGANISM: Homo sapiens

<400> SEQUENCE: 13

Val Glu Val Thr Glu Phe Glu Asp Ile Lys
 1               5                  10

<210> SEQ ID NO 14
<211> LENGTH: 14
<212> TYPE: PRT
<213> ORGANISM: Homo sapiens

<400> SEQUENCE: 14

Ile Asp Phe Tyr Phe Asp Glu Asn Pro Tyr Phe Glu Asn Lys
 1               5                  10
```

```
<210> SEQ ID NO 15
<211> LENGTH: 7
<212> TYPE: PRT
<213> ORGANISM: Homo sapiens

<400> SEQUENCE: 15

Gly Phe Gly Phe Val Thr Phe
1               5

<210> SEQ ID NO 16
<211> LENGTH: 9
<212> TYPE: PRT
<213> ORGANISM: Homo sapiens

<400> SEQUENCE: 16

Gly Gly Gly Gly Asn Phe Gly Pro Gly
1               5

<210> SEQ ID NO 17
<211> LENGTH: 10
<212> TYPE: PRT
<213> ORGANISM: Homo sapiens

<400> SEQUENCE: 17

Val Glu Val Thr Glu Phe Glu Asp Ile Lys
1               5                   10

<210> SEQ ID NO 18
<211> LENGTH: 12
<212> TYPE: PRT
<213> ORGANISM: Homo sapiens

<400> SEQUENCE: 18

Ile Asp Phe Tyr Phe Asp Glu Asn Pro Tyr Phe Glu
1               5                   10

<210> SEQ ID NO 19
<211> LENGTH: 10
<212> TYPE: PRT
<213> ORGANISM: Homo sapiens

<400> SEQUENCE: 19

Glu Phe His Leu Asn Glu Ser Gly Asp Pro
1               5                   10
```

USE OF PROTEIN H AS CYTOSTATIC AGENT

CROSS-REFERENCE TO RELATED APPLICATION

This application is a continuation under 35 U.S.C. §111(a) of International Patent Application No. PCT/GB98/03387, with an international filing date of Nov. 11, 1998, now pending; which application claims the benefit of United Kingdom Patent Application No. 9723724.0, filed Nov. 11, 1997; which applications are incorporated by reference in their entirety.

FIELD OF THE INVENTION

The present invention relates to the use of bacterial proteins. It is based on the finding that protein H, which can be derived from Streptococcus pyogenes, has a cytostatic effect on eukaryotic cells, specifically murine B-lymphocytes. The present invention therefore relates to the use of protein X, and fragments or derivatives thereof, as cytostatic agents, especially in the treatment of diseases involving undesired cell proliferation.

BACKGROUND TO THE INVENTION

Protein H can be obtained from Streptococcus pyogenes, as described in EP-A-0 371, 199 and WO 91/19740. These publications also provide the amino acid sequence of protein H from Streptococcus pyogenes and the sequence of the DNA encoding it. Protein H has a characteristic spectrum of immunoglobulin-binding properties, as described in EP-A-0 371,199 and it is also capable of binding albumin (WO 91/19740). In WO 91/19740, a number of regions within protein H were identified, and designated S, A, B, C1, C2, C3 and D regions. Albumin-binding activity was found to be located in the C and/or D regions.

SUMMARY OF THE INVENTION

We have now found that protein H has a further, and unexpected, property. When biotinylated protein H was incubated with murine B-lymphocytes, it was found that protein H was targeted to the cell nucleus, and inhibited cell proliferation in a dose-dependent manner, although without inducing apoptosis (cell death). Thus, protein H has a cytostatic effect on these cells. We have also observed nuclear targeting of protein H in human T-lymphocytes (Jurkat cells). This suggests that the cytostatic effect may not be confined to B-lymphocytes, but may extend to other eukaryotic cell types as well.

In the cell, protein H was found to interact with actin, and with nucleophosmin/B23, a protein known to shuttle between the nucleus and cytoplasm. In the nucleus itself, protein H was found to interact additionally with the nuclear proteins SET and hnRNP A2/B1, resulting in nuclear accumulation of protein H. We believe that protein H penetrates the cell membrane, becomes associated with nucleophosmin/B23 in the cytoplasm and is transported across the nuclear membrane into the nucleus, where it interacts with SET and hnRNP. As protein H interacts with actin, the actin cytoskeleton may be involved in transporting protein H from the inside of the cell membrane into the cytoplasm, where it becomes associated with NPM/B23. However, the possibility that protein H simply diffuses through the cytoplasm cannot be excluded.

We believe that the interaction with NPM/B23 and/or SET and/or hnRNP A2/B1 may be responsible for the cytostatic effect, although the precise mechanism is not yet fully elucidated. Interactions between protein H and other nuclear components, e.g. nuclear proteins, may also be involved.

The finding that protein H has cytostatic properties was surprising in view of the previously known properties of protein H. Previously, protein H has been known as an immunoglobulin-binding protein, located at the surface of the Streptococcus bacterium, where it protects the bacterium by blocking complement activation at the bacterial cell surface by means of its interaction with the Fc region of IgG. It is therefore surprising that it also appears to effect a further virulence function on behalf of the Streptococcus bacterium, namely a cytostatic effect. It is also surprising that protein H is apparently capable of exerting this effect from the cell nucleus when it has previously been known to exert unrelated effects at the cell surface. By contrast, protein A, an immunoglobulin-binding bacterial cell surface molecule derived from Staphlyococcus aureus, showed no nuclear accumulation. Proteins A and H are functionally similar in that both bind to the same site in the Fc region of IgG. The fact that the functionally similar protein H showed nuclear accumulation is therefore all the more surprising.

Based on our findings, protein H, and fragments and derivatives thereof, can be used to combat undesired cell proliferation, and therefore to treat diseases where undesired cell proliferation takes place. Treatment of tumours of various kinds is one preferred possibility.

Accordingly, the invention provides:

Use of protein H, or a fragment or derivative thereof which is capable of exerting a cytostatic effect on a eukaryotic cell, in the manufacture of a medicament for exerting a cytostatic effect on a eukaryotic cell.

The invention also provides:

A method of exerting a cytostatic effect on a eukaryotic cell comprising administering to said cell an effective non-toxic amount of protein H or a fragment or derivative thereof which is capable of exerting a cytostatic effect on said eukaryotic cell.

BRIEF DESCRIPTION OF THE DRAWINGS

FIG. 1. Binding of protein H to the surface of human peripheral blood lymphocytes and the human Jurkat T cell line determined by FACS analysis.

DETAILED DESCRIPTION OF THE INVENTION

Protein H

Figure 2:
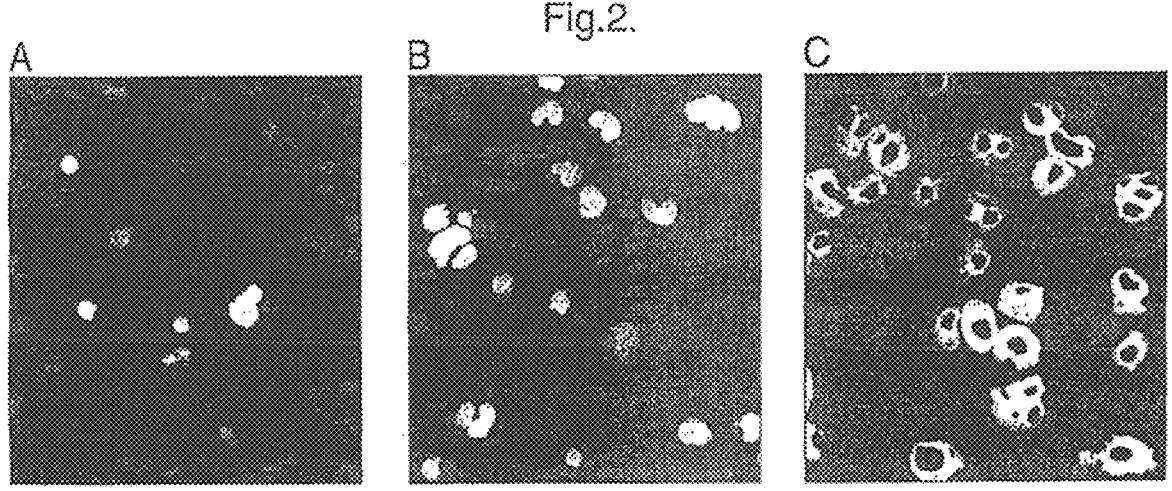
FIG. 2. Uptake and nuclear accumulation of protein H in Jurkat T cells. Depiction of Jurkat T cells incubated with proteins A or H, cytospinned and stained with FITC-avidin. Protein H (A, B) shows nuclear accumulation, protein A (C) does not.

In WO 91/19740, protein H was characterised as having the following domains, from N-terminal to C-terminal: S, A, B, C1, C2, C3 and D. The S domain is a signal peptide which, in nature, is cleaved from the remaining domains before the mature protein (domains A, B, C1, C2, C3 and D) is translocated to and inserted into the bacterial cell wall.

In the Examples below, a shorter version of protein H is used. This lacks the 41 amino acids of the N-terminal S domain and is also truncated by 30 amino acids at the C-terminus. This version of protein H was produced in $E.$ $Coli.$ It is similar to the version of protein H which, in nature, is released from the cell surface of the Streptococcus bacterium by the action of a cysteine protease. The version released by the protease also lacks the S domain and is also truncated at the C-terminus. It is slightly shorter than the version produced in $E.$ $Coli,$ however.

Herein, unless otherwise stated, the term "protein H" means either:

(i) protein H incorporating the signal peptide, as defined in WO 91/19740 and having S, A, B, C1, C2, C3 and D domains and a length of 376 amino acids; or (ii) mature protein H lacking the S domain and having a length of 335 amino acids; or (iii) protein H as produced in $E.$ $Coli,$ lacking the S domain and truncated by 30 amino acids at the C-terminus, and having a length of 305 amino acids; or (iv) protein H as cleaved from the Streptococcus cell surface by the cysteine protease, lacking the S domain and truncated at the N-terminus by a number of amino acids. The precise length of this version of protein H is not yet known, but its molecular mass suggests that the N-terminal truncation is in the order of 50 amino acids, such that it has a length of approximately 285 amino acids. Thus, this version of protein H may, for example have an N-terminal truncation of from 35 to 45, 45 to 50, 50 to 55 or 55 to 65 amino acids, giving it a length, respectively, of 270 to 280, 280 to 285, 285 to 290 or 290 to 300 amino acids.

The full 376 amino acid sequence is given below (see Sequence information section) as SEQ ID No. 6, together with the coding DNA sequence (SEQ ID No. 5). Amino acid No. 1 represents the beginning of the A domain and the boundaries of each region and each version of protein H are indicated on the sequence. In other words, amino acid No. 1 is the first amino acid of the mature protein (version (ii) of protein H as defined above). The numbering differs from that used in WO 91/19740 in that, in WO 91/19740, amino acid No. 1 is the first amino acid of the S domain, which is a signal peptide that is absent from the mature protein.

Protein H can be obtained by the methods described in EP-A-0 371, 199 and WO 91/19740, and can also be produced using the methods of Akesson et al, 1990; and Frick et al, 1994, in combination with the methods described in the Examples. Any of the above-mentioned versions of protein H can also be synthesised by recombinant means, based on the sequences given herein and using standard techniques known in the art (as exemplified, for example, by Sambrook et al, 1989, Molecular Cloning: A Laboratory Manual). The same applies to fragments and derivatives of protein H as defined herein. Similarly, protein H and fragments/derivatives thereof can be prepared synthetically by techniques of peptide synthesis already known in the art. This applies especially to fragments of protein H.

The Cytostatic Effect of Protein H

As described in the Examples, protein H was found to have a cytostatic effect on murine B-lymphocytes, preventing them from proliferating but not inducing apoptosis (cell death). It is not yet clear whether protein H has this effect on all eukaryotic cell types.

According to the invention, protein H, or a fragment or derivative thereof, has a cytostatic effect on a given cell type if it is capable of inhibiting the proliferation of cells of that type. Such inhibition may be complete or partial; i.e. proliferation may be completely prevented or just reduced. The effect may be dose-dependent, in the sense that exposure of cells to higher concentrations of protein H, or a fragment or derivative thereof, may inhibit proliferation to a greater degree. The effect of protein H, or a fragment or derivative thereof, on cell proliferation can be determined by methods known in the art, for example using techniques based on those described in the examples. For example, a person of skill in the art will be able to obtain proliferating cells, optionally by inducing them to proliferate, and expose them to protein H, or a fragment or derivative thereof, optionally in varying concentrations, and observe whether or not they continue to proliferate, or to what extent their proliferation is reduced.

In our experiments, protein H was not observed to cause apoptosis (cell death). According to the invention, it is preferred that protein H and its fragments/derivatives do not cause apoptosis. Thus, preferably the cytostatic effect of protein H or a fragment or derivative of the invention is such that cell growth is inhibited but cell death is not accelerated.

Although it is not yet certain whether protein H is capable of being targeted to the nuclei of all eukaryotic cell types or whether it is selectively targeted to the nuclei of some cell types, it is possible to identify some preferred eukaryotic cell types upon which a cytostatic effect may be exerted.

First, we have observed nuclear targeting of protein H in T-lymphocytes and B-lymphocytes, and a cytostatic effect in B-lymphocytes. Therefore, according to the invention, it is preferred that protein H or a fragment or derivative thereof exerts a cytostatic effect on T-lymphocytes and/or B-lymphocytes.

Further, it is preferred that protein H or a fragment or derivative thereof exerts a cytostatic effect on fibroblasts.

Second, we have observed that protein H interacts with Nucleophosmin (NPM)/B23. As demonstrated by the Examples, it is the AB region of protein H that binds to NPM/B23. NPM/B23 is known to act to shuttle proteins between the cytoplasm and the nucleus. NPM/B23 is ubiquitously expressed but it is up-regulated in certain cell types. In particular, NPM/B23 is more abundant in tumour and proliferating cells than in resting cells. It may be the case that the interaction between protein H and NPM/B23 is responsible, or partly responsible for the cytostatic effect.

For example, it is reasonable to predict that proliferating and tumour cells, having a larger available pool of NPM/

B23, will be more effective in translocating protein H and its fragments or derivatives into the nucleus. Thus, whatever the mechanism of the cytostatic effect, it is reasonable to predict that it will be more pronounced in cells in which NPM/B23 is up-regulated.

Preferred cell types in which NPM/B23 is up-regulated include tumour cells, virus-infected cells and healthy but proliferating cells that show increased levels of NPM/B23.

Some preferred tumours include rapidly proliferating tumours in general; gliomas and other central nervous system tumours such as neuroblastomas; leukaemias; lymphomas; lung tumours; sarcomas; colon tumours such as carcinomas, e.g. low-grade colon tumours that have shown invasion (Duke III–IV); dispersed renal carcinomas; tubal carcinomas, gastric carcinomas; and prostate carcinomas.

Preferred virus-infected cells are cells infected by the human immunodeficiency virus (HIV), for example $CD4^+$ T-cells; or the human Papilloma virus (HPV), for example cervix epithelial cells and prostate epithelial cells; or a Rhinovirus, for example nasal epithelium cells.

Third, we have observed that protein H interacts with protein SET in the nucleus. Notably, the set gene is associated with a chromosomal translocation found in undifferentiated leukaemia that results in its fusion to the can oncogene. However, protein SET is also found in all human cell lines, where it is located, at least predominantly, in the cell nucleus. The fact that it is found in leukaemia cells suggests that it may have a function in cell proliferation and/or differentiation, although this as yet unconfirmed. If protein SET does have such a role, it may be the case that protein H interferes with that role and that this interference accounts, wholly or partially, for the observed cytostatic effect.

If protein H's cytostatic effect is mediated by SET, the fact that protein SET is present in all human cell types suggests that protein H and its fragments and derivatives may be able to exert a cytostatic effect on any cell type. The clear identification of SET in leukaemia cells means that protein H may be particularly effective in exerting a cytostatic effect in leukaemia cells. Thus according to the invention, leukaemia cells are a preferred cell type on which the cytostatic effect may be exerted.

Fourth, we have observed that protein H interacts with hnRNP A2/B1 in the nucleus. hnRNP proteins in general are essential to the biogenesis of mRNA (reviewed by Dreyfuss et al 1993). The various hnRNP proteins bind preferentially to certain RNA species. hnRNP A2/B1 is involved in the transport of certain species of pre-mRNA out of the nucleus, and has been observed to shuttle in and out of the nucleus.

Without wishing to be bound by theory, it is possible to propose some mechanisms by which the interaction between protein H and hnRNP A2/B1 may account for, or contribute to, the cytostatic effect of protein H. Interaction between protein H and hnRNP A2/B1 may lead to sequestration of hnRNP A2/B1 in the nucleus, preventing certain species of mRNA from leaving the nucleus. This could lead to selective inhibition of certain cell functions as synthesis of certain proteins is inhibited. Alternatively, sequestration of hnRNP A2/B1 in the nucleus might interfere with rRNA processing or ribosome assembly, and this may account for, or contribute to, the cytostatic effect.

Taken together, these findings suggest that protein H may exert its strongest cytostatic effect on proliferating cells and/or cells undergoing rapid-growth. In particular, the interaction with hnRNP A2/B1, which is involved in biogenesis of mRNA, points towards this. This is because, in proliferating and growing cells, biogenesis of mRNA is of course more active. Thus, if protein H exerts its cytostatic effect by interfering with biogenesis of mRNA, it will have a more pronounced effect in cells where mRNA biogenesis is more active.

Nuclear Targeting

Based on the experimental results presented herein, protein H is capable of being targeted to the nuclei of eukaryotic cells. Targeting has been demonstrated in T-lymphocytes (Jurkat cells) and B-lymphocytes (Bjab cells).

For the purposes of the invention, protein H and its fragments and derivatives are preferably capable of being targeted to the nuclei of eukaryotic cells. However, it may be the case that it is not essential for nuclear targeting to occur for protein H exerts its cytostatic effect. It should be understood, therefore, that the capacity to be targeted to the nuclei of eukaryotic cells is an optional feature of protein H, and its fragments and derivatives, for the purposes of the present invention.

A person of skill in the art can determine whether or not any given fragment or derivative is capable of being so targeted in any given cell type using techniques based on those described in the Examples. For example, the fragment or derivative can be biotinylated, then incubated with the cells in question. The intracellular distribution of the biotinylated fragment or derivative can then be determined, for example using FITC-Avidin in conjunction with immunofluorescence microscopy. A person of skill in the art will also be able to devise additional methodologies to determine whether or nor protein H or a fragment or derivative thereof is capable of being targeted to the nucleus of any given cell type.

Nuclear localisation has been demonstrated in T-lymphocytes (Jurkat cells) and B-lymphocytes (Bjab cells. It is not yet clear whether protein H is capable of being targeted to the nuclei of all eukaryotic cell types or whether it is selectively targeted to the nuclei of certain cell types, or whether it is targeted to the nuclei of all cell types to some extent but more strongly in certain cell types. However, this can be determined by a person of skill in the art as described above.

Fragments and Derivatives of Protein H

For the purposes of the invention, a derivative of protein H consists essentially of one of the four amino acid sequences defined herein with respect to SEQ ID No. 6 (see sections entitled "protein H" and "sequence information"). For the purposes of the invention, a fragment of protein H is a fragment of any of these four sequences or a fragment of a derivative of any of these four sequences.

For the purposes of the invention, protein H and its fragments and derivatives are capable of exerting a cytostatic effect on a eukaryotic cell, as defined above.

For the purposes of the invention, such fragments and derivatives are preferably capable of being targeted to the nuclei of eukaryotic cells as described above in the section entitled "nuclear targeting".

In accordance with the invention, it is preferred that protein H and its fragments/derivatives are capable of interacting with nucleophosmin/B23. It is also preferred that protein H and its fragments/derivatives are capable of interacting with the nuclear protein SET. It is also preferred that protein H and its fragments/derivatives are capable of interacting with the nuclear protein hnRNP A2/B1. Optionally, protein H and its fragments/derivatives may be capable of interacting with further cytoplasmic and/or nuclear proteins, for example other hNRNPs, or transcription factors. A person of skill in the art can determine whether or not a given fragment/derivative does interact with any of the above-mentioned proteins using techniques based on those given in the Examples.

In particular, a derivative of protein H may be an allelic variant or species homologue of protein H which occurs naturally and is capable of exerting a cytostatic effect on a eukaryotic cell in a substantially similar manner to the four versions of Streptococcus pyogenes protein H as defined herein. Such allelic variants and species homologues will typically be derived from other bacteria, for example, other cocci such as species of Staphylococcus or, preferably, Streptococcus.

Allelic variants and species homologues can be obtained using techniques known in the art, based on the use of probes derived from the Streptococcus pyogenes nucleic acid coding sequence as probes. For example, such a probe can be used to probe libraries made from bacterial cells in order to obtain clones encoding the allelic or species variants. The clones can be manipulated by conventional techniques to express a protein which, according to the invention, is a derivative of protein H.

Preferably, according to the invention, derivatives of protein H have at least 70%, at least 80%, at least 90%, at least 95%, at least 98% or at least 99% homology with one of the four protein H sequences defined herein with respect to SEQ ID No. 6. More preferably, a derivative will have at least 95%, or at least 99% homology with one of those four sequences over a region of at least 20, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology").

The sequence of derivatives of the invention may differ from that of one of the four protein H sequences defined herein with respect to SEQ ID No. 6 by one or more amino acid substitutions. For example, 1, 2, 3, 4, 5 to 10, 10 to 20 or 20 to 30 substitutions may be present, as long as the derivative has the ability to exert a cytostatic effect on a eukaryotic cell in a substantially similar way to protein H. Preferably, substitutions are conservative. For example, conservative substitutions may be made according to the following table. Amino acids in the same block in the second column and preferably in the same line in the third column may be substituted for one another in a conservative manner

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Similarly, derivatives of the invention may show one or more deletions compared to any of the four protein H sequences defined herein with reference to SEQ ID No. 6. Each deletion may be deletion of, for example, 1, 2, 3, 4 or 5 to 10 amino acids.

Similarly, derivatives of the invention may show one or more insertions compared to any one of the four protein H sequences as defined herein with reference to SEQ ID No. 6. Each insertion may comprise, for example, 1, 2, 3, 4, 5 to 10 or 10 to 20 amino acids.

For example, 1, 2, 3, 4, 5 or more such deletions or insertions may be present.

According to the invention, fragments of protein H, and of derivatives as defined above, may be of any length and may be derived from any region of protein H or one of its derivatives, as long as they exert a cytostatic effect. For example, suitable fragments may have a length of from 1 to 20 amino acids, from 20 to 50 amino acids, from 50 to 100 amino acids, from 100 to 150 amino acids, from 150 to 200 amino acids, from 200 to 250 amino acids, from 250 to 300 amino acids, from 300 to 350 amino acids, or greater than 350 amino acids.

We have observed that the binding of protein H to NPM/B23 is mediated by the A region of protein H and the AB region of protein H (i.e. the composite region comprising both the A and B regions). In fact, the AB region binds NPM/B23 more efficiently than complete protein H. It is possible that NPM/B23's interaction with protein H is important to the observed cytostatic effect of protein H (see above) as NPM/B23 is needed to transport protein H into the nucleus. We also believe that it may be the AB region that interacts with protein SET and/or hnRNP A2/B1.

Therefore, fragments of the invention preferably comprise the A region, more preferably the AB region. Optionally, other regions of the protein may also be present. In particular, we believe that the interaction between protein H and actin is mediated by the C-terminal portion of protein H, as competitive binding assays suggest that actin and NPM do not compete for binding to protein H, suggesting that actin binds in a different place to protein H. Therefore, if protein H is transported by means of the actin cytoskeleton, it may be desirable to include the C-terminal portion responsible for actin binding in the fragment. If protein H is capable of reaching NPM in the cytoplasm by diffusion, however, this will be less important.

The AB region of protein H of Streptococcus pyogenes is amino acids 1 to 117 in SEQ ID No. 6. Optionally, all of these 117 amino acids are present. However, a skilled person will also be able to investigate smaller fragments of the AD region to determine whether or not they retain the capacity to be targeted to the nucleus. In particular, recombinant techniques can be used to generate such fragments and techniques based on those given in the Examples can be used to determine whether or not a given fragment is targeted to the nucleus. Therefore, AB fragments may comprise, for example, 1 to 20, 20 to 50, 50 to 80, 80 to 100 or more of the 117 amino acids of the AB region. In such fragments, the AB region may be truncated at its N-terminus by, for example, 1 to 5, 5 to 10, 5 to 20 or 20 to 50 amino acids and/or at its C-terminus by, for example, 1 to 10, 10 to 20 or 20 to 50 amino acids.

As protein H's interaction with protein SET may be important to the cytostatic effect of protein H, it is preferred that fragments and derivatives of the invention have the ability to interact with protein SET in a substantially similar manner to protein H. For example, it is preferred that fragments of the invention include the region(s) of protein H that mediate protein H's interaction with protein SET. A person of skill in the art will be able to determine whether or not a given fragment or derivative has the ability to interact with protein SET using techniques known in the art. In particular, this can be done using techniques based on those of the Examples, e.g by exposing cells to a given fragment or derivatives, suitably labelled, then identifying the proteins that have bound to the labelled fragment or derivative, for example by determination of the molecular weight of these proteins and, if necessary, microsequencing. If protein SET is identified using such a procedure, the fragment or derivative in question has the ability to interact with protein SET.

As protein H's interaction with hnRNP A2/B1 may be important to the cytostatic effect of protein H, it is preferred that fragments and derivatives of the invention have the ability to interact with hnRNP A2/B1 in a substantially similar manner to protein H. For example, it is preferred that fragments of the invention include the region(s) of protein H that mediate protein H's interaction with hnRNP A2/B1. A person of skill in the art will be able to determine whether or not a given fragment or derivative has the ability to interact with hnRNP A2/B1 using techniques known in the art. In particular, this can be done using techniques based on those of the Examples, e.g by exposing cells to a given fragment or derivatives, suitably labelled, then identifying the proteins that have bound to the labelled fragment or derivative, for example by determination of the molecular weight of these proteins and, if necessary, microsequencing. If hnRNP A1/B2 is identified using such a procedure, the fragment or derivative in question has the ability to interact with hnRNP A2/B1.

Further, it is preferred that fragments and derivatives of protein H have the ability to interact with actin, as the interaction between protein H and actin may be important in transport of protein H to the nucleus. A person of skill in the art will be able to determine whether or not a given fragment or derivative has the ability to interact with actin using techniques known in the art. In particular, this can be done using techniques based on those of the Examples.

Optionally, derivatives of the invention may comprise protein H or a fragment of protein H as defined herein, and be extended at either the N or the C-terminus or both by an unrelated amino acid sequence. For example, such a sequence may be of up to 10, up to 20, up to 30, up to 50 or up to 100 amino acids in length, or longer.

Another consideration is the IgG-binding properties of protein H. In general, it is not desirable that fragments/derivatives of protein H retain IgG-binding properties. This is because binding to IgG may lead to the formation of immune complexes which could lead to undesirable side effects and/or reduce protein H's capacity to exert a cytostatic effect. Thus, where protein H or a fragment or derivative is to be delivered by a route that allows the opportunity to form immune complexes (notably intravenous injection), it is preferred to use a fragment or derivative that has no capacity to bind to IgG, or at least has a reduced capacity compared to intact protein H. The IgG binding site is around 20 to 30 amino acids long, and spans the boundary between the A and B regions. Thus, it may be desirable to use a derivative of protein H in which this region is deleted or mutated so that it has no capacity, or a reduced capacity, to bind to IgG. Of course, any such modifications should preferably be made without appreciably disrupting the cytostatic effect. Thus, it is preferred that such derivatives retain the ability to interact with NPM, SET and hnRNP1.

It should also be noted that protein H naturally forms dimers. The dimers have a greater capacity to bind to IgG than isolated protein H monomers. Formation of dimers is favoured below 37° C. (i.e. normal human body temperature)but the dimers are less stable above 37° C. (See, for example, Nilson et al Biochemistry, 1995, 34, pp13688–13698). Thus, the IgG binding capacity of protein H in vivo may actually be lower than in vitro experiments below 37° C. suggest. For this reason, even complete protein H does not necessarily have a great enough IgG binding capacity in vivo to disrupt the cytostatic effect of the invention.

For the purposes of the invention, protein H or a fragment or derivative thereof, may be present in a purely peptidyl form. Alternatively, it may be chemically modified, e.g. post-translationally modified. For example, it may be glycosylated or comprise modified amino acid residues.

Fragments and derivatives of the invention may be synthesised in any suitable manner. Typically, they will be prepared by recombinant means. However, where appropriate, it may also be made synthetically.

Medical Applications of the Invention

The finding that protein H has a cytostatic effect on eukaryotic cells will be useful in combatting a number of diseases of the human or animal body.

In particular, protein H and its fragments and derivatives will be useful in treating diseases of proliferating cells, or diseases that involve undesired cell proliferation. In particular, protein H and its fragments and derivatives can be used to exert a cytostatic effect on tumour cells, thereby preventing growth of the tumour. Tumours which can be treated according to the invention include tumours in which NPM/B23 is up-regulated.

Some preferred tumours include rapidly proliferating tumours in general; gliomas and other central nervous system tumours such as neuroblastomas; leukaemias; lymphomas; lung tumours; sarcomas; colon tumours such as carcinomas, e.g. low-grade colon tumours that have shown invasion (Duke III–IV); dispersed renal carcinomas; tubal carcinomas, gastric carcinomas; and prostate carcinomas.

Similarly, protein H and fragments/derivatives thereof of can be used to suppress the proliferation of virus-infected cells, thus combatting the viral infection. Preferred virus-infected cells are cells infected by the human immunodeficiency virus (HIV), for example $CD4^+$ T-cells; or the human Papilloma virus (HPV), for example cervix epithelial cells and prostate epithelial cells; or a Rhinovirus, for example nasal epithelium cells. Thus, protein H or a fragment or derivative thereof, can be used to combat infection by one of these viruses.

Further, protein H may be useful in treating inflammatory conditions, as inflammatory conditions commonly involve cell proliferation. Examples of such inflammatory conditions include arthritis, particularly rheumatoid arthritis; arteritis; chondritis; colitis; dermatitis; enteritis; myositis; tendosynobitis; and autoimmune inflammatory conditions such as SLE (systemic lupus erythematosis).

The use of protein H and its fragments and derivatives in the treatment of a condition may be combined with other treatments. In particular, where treatment of a tumour is desired, it may be combined with or used in association with other chemotherapeutic or chemopreventive agents for providing therapy against tumours. Similarly, it may be combined with the use of other agents for treatment of viral infections or other conditions.

For example, the inventors have found that protein H and NPM interact. NPM expression has been found to be hormone sensitive in certain cell types, including human vascular smooth muscle cells and rat prostate cells. This suggests that treatment with an appropriate hormone in conjunction with protein H or a fragment or derivative of the invention may increase uptake of protein H or a fragment or derivative of the invention, leading to a greater cytostatic effect. As NPM expression has been found to be hormone sensitive in rat prostate cells, it may, in particular, be appropriate to carry out this type of treatment on prostate carcinomas.

Pharmaceutical Compositions

According to the invention, protein H or a fragment or derivative thereof will typically be used in the form of a pharmaceutical composition comprising the protein H or fragment/derivative thereof and a pharmaceutically acceptable carrier or diluent.

Any suitable pharmaceutical formulation may be used. For example, suitable formulations may include aqueous or non-aqueous sterile injection solutions, which may contain anti-oxidants, buffers, bacteriostats, bactericidal antibiotics and solutes which render the formulation isotonic with the bodily fluids of the intended recipient; and aqueous and non-aqueous sterile suspensions which may include suspending agent and thickening agents. Some preferred formulation ingredients include mannitol or another sugar and/or phosphate-buffered saline (PBS).

It should be understood that in addition to the ingredients particularly mentioned above, the formulations of this invention may include other agents conventional in the art having regard to the type of formulation in question.

Dosage Information

According to the invention, any effective, non-toxic amount of protein H or a fragment or derivative thereof may be administered to a patient. The dose of protein H or a fragment or derivative thereof may be adjusted according to various parameters. Such parameters include, for example, the age, weight and condition of the patient to be treated, the mode of administration used, the condition to be treated, the efficiency of the particular protein H, derivative or fragment being used in achieving a cytostatic effect in the cell type concerned and the required clinical regimen.

As a guide, it appears that $10^6$ B-lymphocytes accumulate in the region of 1 ng to 10 ng of protein H in their nuclei. This suggests that the amount administered may be such that the dose comprises $10^{-15}$ g to $10^{-9}$ g of protein H or a fragment or derivative thereof per cell to which delivery is desired, for example $10^{-14}$ g to $10^{-8}$ g, e.g. in the region of $10^{-14}$ g, $10^{-13}$ g, $10^{-12}$ g, $10^{-11}$ g, $10^{-10}$ g, $10^{-9}$ g or $10^{-8}$ g per cell. The amount of protein H or a fragment/derivative thereof thus depends on what cells it is desired to deliver the protein or fragment/derivative to, and how many of them there are.

For example, a typical dose might be 1 to 1000 μg of protein H or a fragment/derivative thereof, for example 1 to 10 μg, 10 to 100 μg or 100 to 1000 μg.

These dosages are intended only as a guide since a skilled medical practitioner will be able to determine readily the most appropriate dosage for any particular patient and condition.

Similarly, the skilled medical practitioner will be able to determine the appropriate dosage schedule, which will vary according to the factors given above in respect of dosage amounts. However, single doses and multiple doses spread over periods of days, weeks or months are envisaged.

Routes of Administration

According to the invention, protein H or a fragment or derivative thereof can be formulated for clinical administration by mixing with a pharmaceutically acceptable carrier or diluent, as described above. For example, they can be formulated for topical, parenteral, intravenous, intramuscular or transdermal administration. Of course, the route of administration will be tailored to the particular condition to be treated.

For example, where complete protein H, or a fragment/derivative comprising the IgG binding site is used, it may not be desirable to inject the protein or fragment/derivative intravenously, as this may lead to the formulation of immune complexes of protein H and IgG. In these situations, other means of administration are preferred, e.g. direct delivery of the protein or fragment/derivative to the site where it is needed. For example, in the case of a tumour, it is desirable to inject the protein or fragment/derivative directly into the tumour. However, as noted above, even the IgG binding capacity of complete protein H is not necessarily enough to disrupt the cytostatic effect of the invention.

EXAMPLE

The following Example illustrates the invention.

Summary

Some strains of the human pathogen *Streptococcus pyogenes* express a surface protein called protein H, which is released from the streptococcal surface by a cysteine proteinase produced by the bacteria. Here we find that soluble protein H binds to the surface of lymphocytes and granulocytes. The molecule is taken up by lymphocytes and transported to the nucleus through a previously unknown intracellular pathway. In the cytoplasm, protein H was found to bind to actin whereas when proteins were solubilised from membrane fractions by papain, protein H was found to interact with nucleophosmin/B23, a protein known to shuttle between the nucleus and the cytoplasm. In the nucleus, protein H is dissociated from nucleophosmin/B23 and instead forms complexes with the nuclear proteins SET and hnRNP A2/B1, resulting in nuclear accumulation of protein H and a cytostatic effect.

Experimental Procedures

Bacterial Strain, Proteins, Bacterial Expression, in vitro Translation, Labelling of Proteins, Coupling of Proteins to Sepharose The group A streptococcal strain AP1 of serotype M1 (Akesson et al., 1994) was used. Recombinant protein H and peptide fragments corresponding to the AB and A regions of protein H have been described (Akesson et al., 1990; Frick et al., 1994). For the generation of in vitro translated NPM, RNA was prepared from Jurkat T cells using RNazol B (Tel-Test Inc., Friendswood, USA) according to the manufacturer's recommendations. cDNA synthesis was performed by incubation of 5 μg RNA with 1×RT buffer (Gibco BRL), 1 mM dNTP, 10 mM DTT, 0.1 mg BSA/ml, 4.5 μM poly $dT_{18}$, 20 U RNase inhibitor (Boehringer Mannheim) and 200 U M-MLV reverse transcriptase (Gibco BRL) in a final volume of 50 μl for 37° C. for 1 hour. NPM was PCR amplified using the 5' primer containing a NarI site 5'-GCAGGGCGCCATGGAAGATTCGATGGACAT-3' (SEQ ID No. 1) and the 3' reverse primer 5'-CAG GAATTCTTATTAAAGAGACTTCCTCCACTGCC-3'(SEQ ID No. 2) containing an EcoRI site. For the generation of NPM peptide fragments by in vitro translation two additional oligonucleotides were used for PCR amplification: The $NH_2$-terminal peptide was generated with the reverse primer 5'-CAGGAATTCTTATTAGCTACCACCTCCAGGG-3' (SEQ ID No. 3) and the primer 5'-TTGATGAAGGTTCCACAGAAAAAAGTAAAACT TGCTG-3' (SEQ ID No.4), was used for the COOH-terminal peptide. The PCR products were blunted and cut with EcoRI, whereas the vector pGem-3Z was cut with HincII/EcoRI, and both were ligated. In vitro translation was done using TNT Coupled Reticulocyte Lysate Systems (SDS, Falkenberg, Sweden) according to the manufacturer's recommendations. Recombinant protein A was purchased from Pharmacia Biotech, Uppsala, Sweden, and actin from porcine heart was from Sigma (MO., USA). Protein H was labelled with $^{125}I$ using the Bolton and Hunter reagent (Amersham, UK). Protein fractions 85–87 purified with FPLC were concentrated in an Amicon centricon concentrator (Amicon, Inc., Beverly, Mass.), and labelled with $^{125}I$ using the chloramine T method (Greenwood et al., 1963). $^{125}I$ was from Nordion Int. Co. (Canada). Protein H was dialyzed against 0.1 M $NaHCO_3$ pH 8.3+0.5 M NaCl, and coupled to CNBr-activated Sepharose 4B (Pharmacia Biotech) as previously described (Frick et al., 1995).

Electrophoresis and Western Blot Analysis

SDS-PAGE was performed as described by Laemmli (1970), using a total polyacrylamide concentration of 10% or 13.6% and 3.3% crosslinking. Samples were boiled for 3 minutes in a buffer containing 2% SDS and 5% 2-mercaptoethanol. Gels were fixed with a mixture of 7% acetic acid and 10% ethanol, dried and autoradiographed. Molecular weight markers were from Sigma. Gels were stained with Coomassie Blue. Protein fractions were applied to PVDF membranes (Immobilon, Millipore, Bedford, Mass., USA) using a Milliblot-D system (Millipore). Membranes were blocked at room temperature for 1 hour in VBS (10 mM veronal, 0.15 M NaCl pH 7.4) containing 0.25% Tween-20 and 0.25% gelatin. After incubation at room temperature for 3 h with radiolabelled protein in VBS containing 0.1% gelatin, the membranes were washed four times with 1.0 M NaCl, 10 mM EDTA, pH 7.7, 0.25% Tween-20 and 0.25% gelatin. The filters were air-dried and autoradiographed at −70° C. using Kodak X-Omat AR films and Kodak X-Omat regular intensifying screens.

Cells and Preparation of Proteins from Membrane Fractions from the Jurkat Cell Line For flow cytometric analysis human peripheral blood lymphocytes (PBL) from healthy volunteers were depleted from erythrocytes and prepared by Ficoll separation (Pharmacia Biotech). Jurkat cells, a human T cell line, were cultured in RPMI 1640 supplemented with 7.5% FCS and 20 mM sodium pyruvate. Membrane preparations were performed in the cold (0–4° C.). $10^9$ Jurkat cells were homogenized in homogenization buffer (0.05 M Tris-HCl pH 7.5, 0.25 M sucrose, 0.005 M $MgCl_2$, 0.025 M KCl ) followed by centrifugation at 1000×g for 10 min. The supernatant was further centrifuged at 105000×g for 45 min. This supernatant was saved and used as a cytoplasmic fraction whereas the pellet obtained was solubilised in 4 ml 0.01 M Tris-HCl pH 8.0. The protein content was determined with the Coomassie protein assay reagent (Pierce, Boule Diagnostics AB, Huddinge, Sweden). After addition of 0.2 mg papain (Sigma) per mg protein solution, and L-cysteine (Sigma) to a final concentration of 4 mM, the mixture was incubated at 37° C. for 45 minutes. To terminate the reaction, 4 ml ice-cold 0.01 M Tris-HCl pH 8.0 and iodacetamide (Sigma) to a final concentration of 6 mM were added, followed by centrifugation for 1 hour at 105000×g. Papain was removed from the supernatant by chromatography on DEAE Sephadex A-50 (Pharmacia Biotech) equilibrated with 20 mM Tris-HCl, pH 8.0. The column was washed with 5 volumes 20 mM Tris-HCl pH 8.0, and the material was eluted with 3 volumes of a 0.5 M NaCl in this buffer followed by dialysis against 20 mM Tris-HCl pH 8.0. For fractionation of the papain digested membrane proteins, the solution was loaded onto an ion-exchange column (Mono-Q, Pharmacia Biotech) mounted on a fluid pressure liquid chromatograph (FPLC, Pharmacia Biotech). Elution was performed with a 70 ml linear salt gradient (from 0 to 1 M NaCl in 20 mM Tris-HCl pH 8.0). Fractions of 0.5 ml were collected. Murine splenic B cells from Balb/c mice were isolated as previously described (Axcrona et al., 1995). Lymphocytes at $3×10^5$/ml were plated out in 96 well plates. B cells were activated with LPS (25 µg/ml, Difco) and incubated with proteins H and A at indicated concentrations. One µCi [3H]thymidine was added per well for the last 4 hours of a 40 hour culture period, cells were harvested and processed for scintillation counting. Values are mean+/−SD of duplicates. For preparation of nuclear and cytoplasmic extracts from murine B cells, cells were activated for 24 hours at $3.8×10^6$ cells/ml with LPS (25 µg/ml) and protein H at 100 µg/ml.

Preparation of Nuclear Extracts from Jurkat T Cells and Murine B Cells

Nuclei from Jurkat cells were isolated as described by (Mirkovitch et al., 1984). Preparations of nuclei were resuspended in 100 µl of buffer A (50 mM Hepes buffer, 50 mM KCl, 0.1 mM EDTA, 1 mM PMSF, 1 mM DTT, 10% glycerol) and additional buffer A was added to a final volume of 162 µl. 13 µl of 4 M $(NH_4)_2SO_4$ was added to bring the final concentration to 0.3 M. The cells were rocked for 30 minutes and the viscous material was transferred to a 0.2 ml TLA-100 tube (Beckmann), followed by centrifugation at $10^5$ rpm for 10 minutes. 125 µl of the supernatant was transferred to a second TLA-100 tube, 75 µl of 4 M $(NH_4)_2SO_4$ was added to increase the final concentration to 1.5 M. The solution was centrifuged at 50000 rpm for 5 minutes. The supernatant was removed and the pellet was resuspended in 100 µl of buffer A. Extracts were used immediately or stored at −80° C.

Affinity Chromatography, Competitive Binding Assay, and Plasmon Resonance Spectroscopy The $^{125}$I-labelled pooled fractions 85-87 from Mono-Q and in vitro translated NPM peptides were applied onto a Protein A-Sepharose column (Pharmacia Biotech) and the flowthrough fractions were run on a protein H-Sepharose column. The column was extensively rinsed with PBSAT (PBSA+0.05% Tween-20). Bound proteins were eluted with 3 M KSCN and the radioactivity of the fractions was measured in a gamma counter. Fractions were also analysed by SDS-PAGE. Competitive binding assays were performed as reported (Åkerström and Björck, 1989). Binding kinetics were determined by surface plasmon resonance spectroscopy using a BIACORE X system (Biacore AB, Uppsala, Sweden). Actin and nuclear extracts purified on protein H-Sepharose were immobilized on research grade CM5 sensor chips in 10 mM sodium acetate at pH 4.0 and 4.5, respectively, using the amine coupling kit supplied by the manufacturer, whereas biotinylated NPM was coupled to CM5 sensor chips precoupled with avidin (Biacore). All measurements were carried out in PBST. Analyses were performed at 25° C. and at a flow rate of 10 µl/min. To calculate dissociation and affinity constants, 35 µl of protein H or proteins A, H or actin were applied in serial dilutions (2n; starting at 600 µg/ml). Surfaces were regenerated with 35 µl 1 M KSCN at a flow rate of 10 µl/min. The kinetic data were analysed by the BIAevaluation 2.2 program (Biacore).

Amino Acid Sequence Analysis

Proteins were separated by SDS-PAGE and stained with Coomassie Blue. Protein bands were excised and digested in-matrix using trypsin. Peptide fragments were separated by reverse-phase HPLC (Vydac 218TP, I.D. 1.6×250 mm) and aliquots were analysed by automated Edman degradation using a model 477A sequenator connected to a model 120A on-line PTH-analyser (Applied Biosystems, Weiterstadt, Germany) and by mass analysis using cyano-4-hydroxycinnamic acid as a matrix on a Voyager-DE MALDI-TOF mass spectrometer (Perseptive Biosystems, Wiesbaden, Germany) (Herrmann et al., 1996; Herwald et al., 1996). The Blast network server at the National Center for Biotechnology Information (Altschul et al., 1990) was used for sequence homology searching.

Antibodies, Flow Cytometrical and Fluorescence Microscopical Analysis

For flow cytometric analysis of human PBL, mouse anti-human CD3, CD4, HLA-DP/DQ/DR (Becton Dickinson, San Jose, Calif., USA) and CD8 antibodies (Dako Patts, Gentofte, Denmark) were used. As a positive and negative control for Jurkat T cells, an isotype control set of a y1-FITC, y2-PE and anti-CD45 PerCP (Becton Dickinson) labelled antibodies were used, where the y1/y2 antibodies were unspecific fluorochrome-conjugated antibodies. Proteins H and A were biotinylated as previously described (Axcrona et al., 1995), and used in conjunction with FITC-coupled avidin (Sigma). Mouse anti-human HLA-DP/DQ/DR antibodies were detected with goat anti-mouse FITC-coupled antibody (Becton Dickinson). FACS-analysis was performed on a Becton Dickinson FACSort flow cytometer (Becton Dickinson). Each dot blot and histogram represents the analysis of $10^4$ gated cells. For fluorescence microscopy 0.5×10 Jurkat cells were incubated with 20 μg biotinylated proteins in culture medium for 30 minutes on ice in a flat bottomed 96 well plate. Cells were washed once, followed by continued incubation in a culture chamber at 37° C. for the indicated times. The cells were washed twice in 4 ml PBS, taken up in 400 μl PBS, centrifuged on slides in a cytocentrifuge (Shandon, Cytospin 2) at 550 RPM for 3 minutes. After incubation with FITC-coupled Avidin (Sigma), the cells were examined in a fluorescence microscope (Leica Aristoplan) and photographed.

Experimental Procedures Using Anti-protein H Anti-NPM Antibodies

Preparation of Anti-protein H F(ab')2 fragments

Anti-protein H antiserum was applied to a protein G-Sepharose column. The column was extensively washed with PBS and bound IgG was eluted with 0.1 M glycin-HCl pH 2.0. Eluted IgG was dialyzed against acetate buffer pH 4.5 (70 mM CH$_3$COONa—50 mM HCl ) followed by proteolytic cleavage with pepsin (ratio of protein:pepsin was 100:1) for 21 hours at 37° C. The reaction was terminated by raising the pH of the solution to 7.5 with 1 M Tris and uncleaved IgG was removed by subjecting the material to affinity chromatography using protein G-Sepharose. Unbound material corresponding to polyclonal anti-protein H F(ab')$_2$ fragments was collected and dialyzed against PBS. Coupling of F(ab')$_2$ fragments to Sepharose 4B (Pharmacia Biotech) was performed as recommended by the manufacturer.

Cloning and Expression of Nucleophosmin (NPM)

For expression in *E. coli* NPM was PCR amplified using the 5' primer containing an EcoRI site 5'-GCAG GAATTCATGGAAGATTCGATGGACAT-3' (SEQ ID No 7) and the 3' reverse primer 5'-ATA GCGGCCGCTTATTAAAGAGACTTCCTC-3'(SEQ ID No 8) containing a NotI site. The DNA was cloned into the prokaryotic expression vector pGEX-6p-1 (Pharmacia Biotech) using the EcoRI and NotI sites. Recombinant NPM fused to Glutathione S-transferase (GST) was expressed and purified according to the manufacturers instructions. After purification on Glutathione Sepharose, the GST tag was cleaved off using PreScission$^a$ Protease (Pharmacia Biotech). From 1 l of an over night culture, approximately 1 mg pure NPM was achieved. Antibodies against NPM were raised in rabbits. ps Preparation of Cytoplasmic and Nuclear Extracts from Jurkat T Cells and Detroit Cells Jurkat T cells and Detroit 562 human (carcinoma) pharynx epithelial cells (ATCC CCL 138), incubated with various proteins, were washed five times with PBS, resuspended in buffer A (10 mM Hepes, 15 mM KCl, 2 mM MgCl$_2$, 1 mM DTT, 0.1 mM EDTA, 1 mM PMSF, 1 μantipain/ml, 0.5 μg leupeptin/ml) and the cell membranes were lysed using 0.2% NP-40. The cytoplasmic fractions were collected after centrifugation at 1000×g for 10 min and the nuclear pellets were washed twice with PBS and resuspended in 100 μl of buffer B (50 mM Hepes buffer, 50 mM KCl, 0.1 mM EDTA, 1 mM PMSF, 1 mM DTT, 10% glycerol). Additional buffer B was added to a final volume of 162 μl and 13 μl of 4 M (NH$_4$)$_2$SO$_4$ was added to bring the final concentration to 0.3 M. The resuspended nuclei were rocked for 30 min at 4° C. and the viscous material was transferred to a 0.2 ml TLA-100 tube (Beckmann), followed by centrifugation at 350 000 ×g for 10 min. The supernatants corresponding to the nuclear fractions were collected and both cytoplasmic and nuclear fractions were subjected to immunoprecipitation.

Immunoprecipitation

Extracts prepared from Jurkat cells, incubated with protein H or protein L (150 μg) for 16 hours at 37° C., were immunoprecipitated by using polyclonal antibodies against protein H or protein L, 2 μl respectively, for 2 hours at 4° C. 40 μl protein A-Sepharose was added and incubation was continued for 16 hours at 4° C. Extracts from Detroit 562 cells, incubated with protein H were immunoprecipitated similarly.

Alternatively extracts from Jurkat cells, incubated with protein H (150 μg) for various timepoints at 37° C., were precleared with 50 μl glycine-Sepharose, for 2 hours at 4° C., followed by immunoprecipitation using polyclonal anti-protein H F(ab')$_2$-Sepharose (100 μl) for 16 hours at 4° C.

The Sepharose pellets were then washed three times with PBS, boiled for 3 min in buffer containing 2% SDS and 5% 2-mercaptoethanol followed by centrifugation at 8000×g for 5 min. Supernatants were recovered and subjected to SDS-PAGE and Western blot analysis. Membranes were blocked at 37° C. in PBST (PBS+0.05% Tween-20) containing 5% skim milk and probed with polyclonal antibodies followed by peroxidase-conjugated protein A and developed with ECL.

Results

Protein H Interacts with Human Lymphocytes and Granulocytes

Protein H is released from the streptococcal surface through the action of a cysteine proteinase produced by the bacteria (Berge and Bjorck, 1995). The *E. coli*-produced fragment of protein H used in this study is similar in size to the fragment released by the streptococcal enzyme, and in the following Examples protein H refers to this COOH-terminally truncated fragment expressed by and purified from *E. coli*. The interaction of protein H with the surface of T cells and granulocytes was analysed with flow cytometry. Human peripheral blood lymphocytes were incubated with protein H and the majority (>90%) of the CD3', CD4$^+$ and CD8$^-$ cells bound protein H (FIG. 1A). When the binding of protein H to cells within the granulocyte gate was analysed, protein H also stained these cells brightly (FIG. 1A). Protein H binds to IgGFc (Frick et al., 1994) and previous work has indicated affinity also for human MHCII antigens (Åkesson et al., 1994). The human Jurkat T cell line was therefore chosen for the subsequent experiments as MHC II expression on these cells could be excluded with flow cytometry. More than 97% of the Jurkat T cells were found to be protein H$^+$ as compared to the FITC avidin background. Furthermore, as shown in FIG. 1B, Jurkat cells were stained by anti-CD45 but not with unspecific γ1 FITC/γ2 PE mouse mAbs.

Protein B is Taken Up By Lymphocytes and Accumulated in the Nucleus

Biotinylated protein H was incubated with Jurkat cells for different timepoints. Following incubation, cells were cytospinned, fixed, and FITC-coupled avidin was added. As demonstrated by immunofluorescence microscopy (FIG. 2) protein H was gradually accumulated in the nuclei, and after 8 hours 80% of the nuclei showed staining. In contrast, cytoplasmic staining but no labelling of nuclei was detected when the Jurkat cells were incubated with biotinylated protein A (FIG. 2C). Like protein H, protein A of *Staphylococcus aureus* is an IgGFc-binding bacterial surface molecule. Previous work has demonstrated that protein H binds to murine and human B cells (Axcrona et al., 1995) and as in the case of Jurkat cells, protein H was targeted to the nuclei of the human B cell line Bjab, whereas protein A showed no nuclear accumulation.

Protein H is Taken Up By Lymphocytes and Epithelial Cells $5 \times 10^6$ Jurkat cells were separately incubated with 150 µg of protein H or protein L for 16 hours. Cytoplasmic and nuclear extracts were prepared and immunoprecipitation was performed using polyclonal antibodies against proteins H and L, respectively, followed by the addition of protein A-Sepharose. Precipitated materials were run on SDS-PAGE and blotted to PVDF membranes. The membranes were probed with polyclonal antibodies against proteins H and L, respectively, followed by peroxidase-conjugated protein A and developed with ECL. Protein H was taken up by the cells and could be detected in both cytoplasmic and nuclear extracts, whereas protein L was not taken up by the cells (not shown).

Epithelial cells (Detroit 562) were also incubated with protein H (150 µg) and extracts prepared from these cells were immunoprecipitated as described above. Protein H was taken up by the Detroit cells, although a lower amount of protein was detected in the nuclear extracts.

Protein H Interacts with Nucleophosmin/B23 and actin

Figure 3:
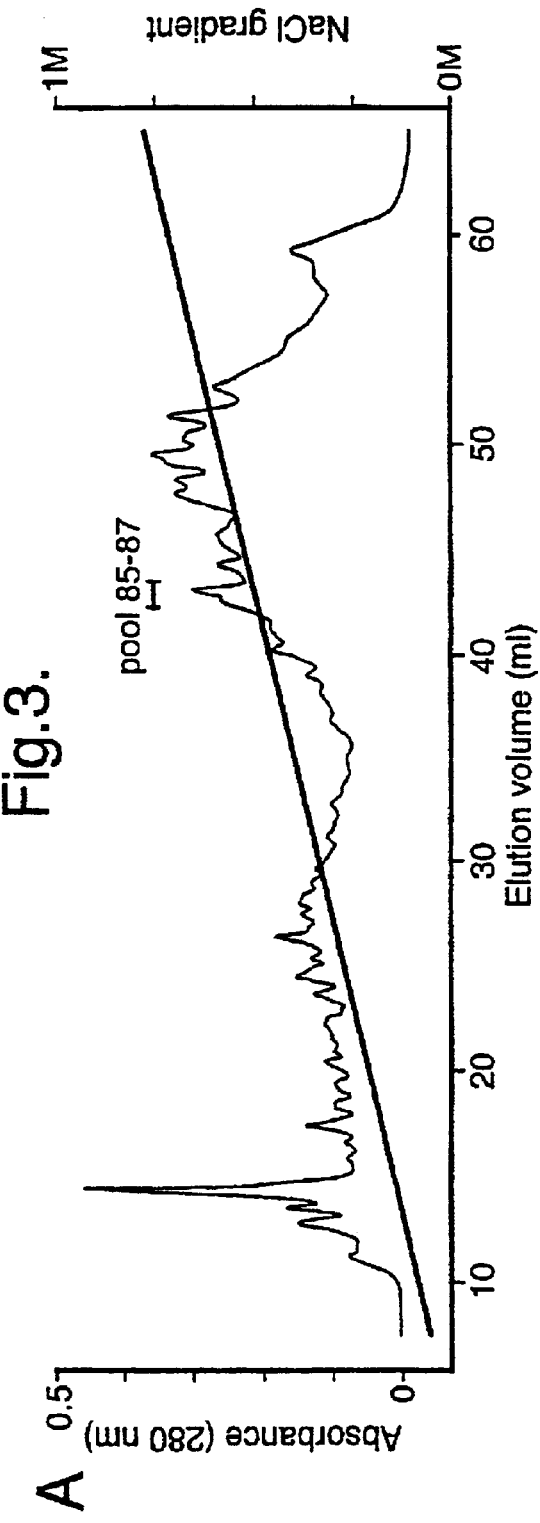
FIG. 3. Protein H interacts with nucleophosmin. (A) Results of FPLC on mono-Q column of Jurkat T cells digested with papain and solubilised. (B) Results of radio-labelled pool 85-87 material from (A) being run on protein A-Sepharose (left) and the pooled fractions of the run-through peak from protein A-Sepharose being subjected to a protein H-Sepharose column (right). (C) Identification of NPM in pool 85-87 material from (A) (SEQ ID NOS: 9–11). (D) Comparison of SDS PAGE of in vitro translated and $^{35}$S-methionine-labelled NPM peptides (left) and SDS-PAGE of the same peptides when applied to protein H-Sepharose. (E) Mapping of the NPM-binding region of protein H by competitive inhibition.
Figure 3:
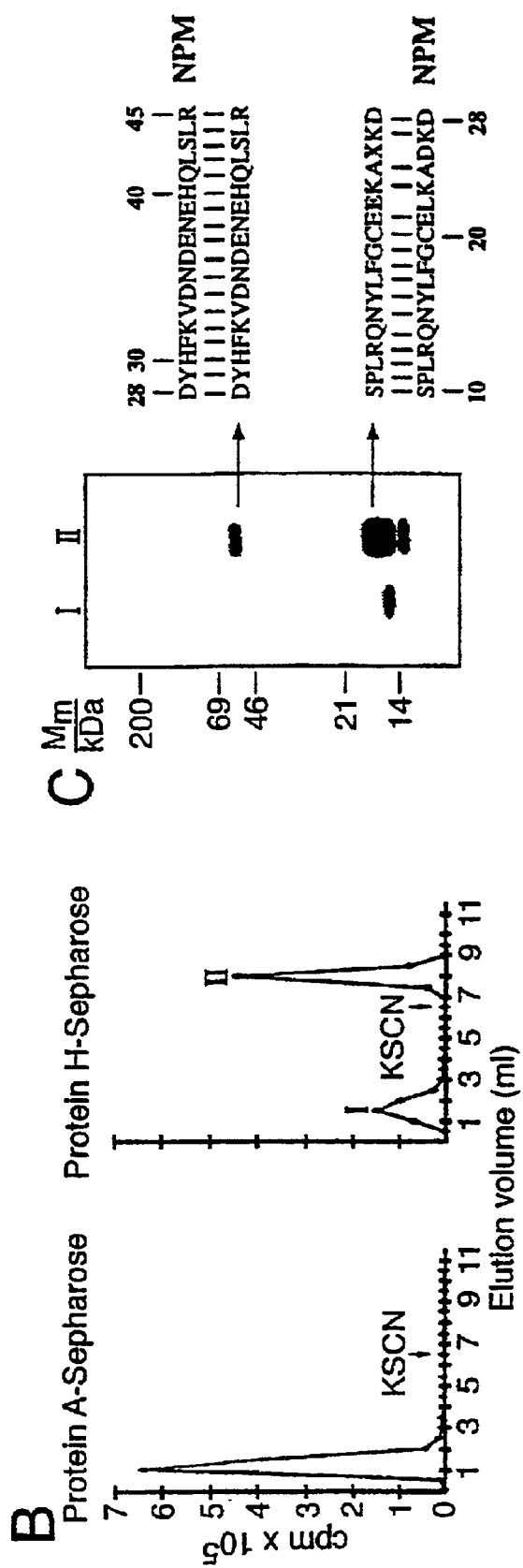
Figure 3:
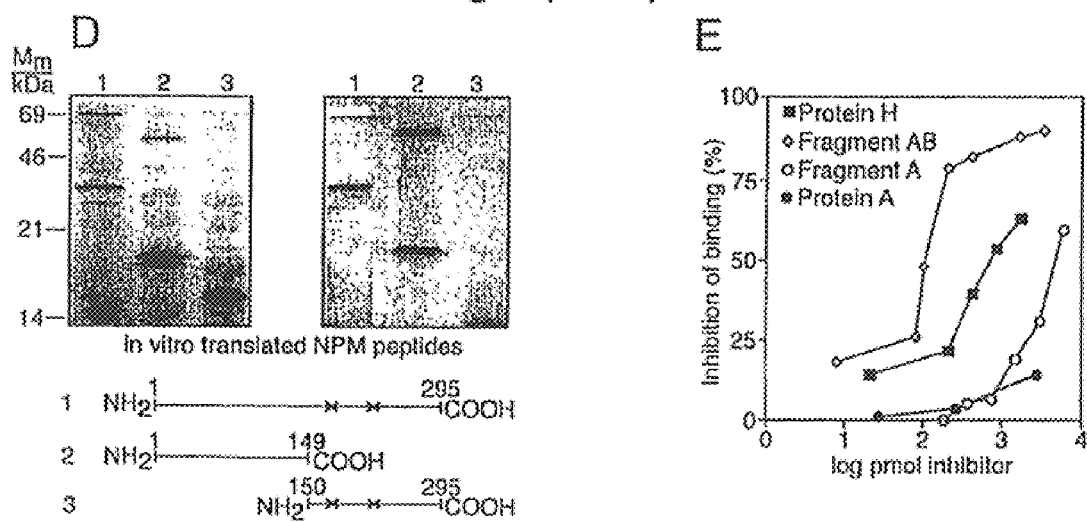

To identify proteins interacting with protein H and mediating its uptake, membrane preparations obtained by subcellular fractionation of Jurkat cells were treated with detergent (NP-40). However, no protein H-binding proteins could be detected in this solubilised material before or following purification by ion-exchange chromatography, gel filtration or affinity chromatography on protein H-Sepharose. To release water soluble peptides from Jurkat cell membrane preparations, papain was used. The solubilised peptides were separated by ion-exchange chromatography and fractions were eluted by a linear sodium chloride gradient (FIG. 3A). The fractions were applied in slots to PVDF membranes and probed with radiolabelled protein H. Fractions 85-87 reacted with the probe, and they were pooled. A portion (20 ml) was labelled with $^{125}$I and subjected to affinity chromatography on protein A-Sepharose (FIG. 3B). The labelled peptides showed no affinity for protein A but when the run-through fractions from protein A-Sepharose were applied to protein H-Sepharose more than 70% of the radioactivity was bound and eluted with 3M KSCN (FIG. 3B). When analysed by SDS-PAGE and autoradiography, this material (peak II) contained two major bands of 18 and 54 kDa, respectively. The run-through material (peak I) gave rise to a single band with a molecular mass of approximately 16 kDa. Unlabeled pool 85-87 material was now purified on protein H-Sepharose followed by SDS-PAGE. After staining, the 18 and 54 kDa bands (see FIG. 3C) were cut out of the gel, digested with trypsin and separated by HPLC. The amino acid sequences shown in FIG. 3C could be determined from HPLC peaks and demonstrated that both bands contained nucleophosmin/B23 (NPM), a protein known to shuttle between the cytoplasm and the nucleus (Borer et al., 1989). Monomeric NPM has a molecular mass of 32 kDa but the protein is known to form oligomers (Schmidt-Zachmann et al., 1987; Herrera et al., 1996), including diners of 70 kDa also under denaturing conditions (see Umekawa et al., 1993 and FIG. 3D). Therefore the 54 kDa band probably consists of dimers of NPM fragments generated by papain cleavage whereas the 18 kDa fragments do not form multimers in SDS-PAGE. Intact NPM and two fragments of NPM covering the $NH_2$- and COOH-terminal halves of NPM, respectively, were generated by PCR and in vitro translation. These $^{35}$S-methionine-labelled peptides were separated by SDS-PAGE followed by autoradiography (FIG. 3D, left). As mentioned above, NPM has a tendency to form dimers-oligomers (Schmidt-Zachmann et al., 1987; Umekawa et al., 1993; Herrera et al., 1996). This property is evident for the intact molecule giving rise to bands of 35 and 70 kDa corresponding to monomers and dimers. In case of the $NH_2$-terminal fragment with an apparent molecular mass of 18 kDa, a band corresponding to a trimer of 54 kDa is seen, whereas no distinct oligomers are present in lane 3 where the COOH-terminal fragment was run. This is consistent with previous observations demonstrating that the COOH-terminal part of NPM is not essential for oligomerization (Herrera et al., 1996). When the three NPM peptides were subjected to affinity purification on protein H-Sepharose, intact NPM and the $NH_2$-terminal fragment bound to protein H. The COOH-terminal fragment, however, did not show affinity for protein H-sepharose (FIG. 3D, right). These results and the fact that the 18 kDa $NH_2$-terminal papain fragment of NPM shown in FIG. 3C, also has affinity for protein H, map the binding of protein H to the $NH_2$-terminal part of NPM. As the COOH-terminal region of RPM contains the signals essential for its localization to the nucleolus (Wang et al., 1993), binding of protein H should not interfere with the targeting of NPM.

Using fragments of protein H in competitive binding experiments the region of protein H interacting with NPM was identified. Protein H was immobilized on Sepharose and radiolabelled NPM (pool 85-87) was added. 80–90 percent of the radioactivity was bound to the Sepharose. As demonstrated in FIG. 3E this binding was inhibited by unlabeled protein H and by fragments A and AB of protein H, whereas the effect of protein A was at background level also at high concentration. The inhibition with the $NH_2$-terminal fragment AB, which is an even more efficient inhibitor than intact protein H, maps the binding of NPM to this region.

The membrane material subjected to papain digestion was obtained by a two-step centrifugation procedure where the supernatant following the final centrifugation at 105000 g represents a cytoplasmic fraction. Also this material was subjected to affinity chromatography on protein H-Sepharose. A dominating band with an apparent molecular mass of 40 kDa was eluted, and $NH_2$-terminal amino acid sequencing established that the band was actin.

Nucleophosmin is Coprecipitated with Protein H $1 \times 10^6$ Jurkat cells were incubated with protein H (150 µg) for various timepoints and in order to analyse if nucleophosmin could be coprecipitated with protein H, nuclear extracts were prepared. The extracts were precleared with glycine-Sepharose and immunoprecipitated using anti-protein H F(ab')$_2$-Sepharose. Precipitated materials were run on SDS-PAGE and blotted to a PVDF membrane. The membrane was probed with polyclonal antibodies against recombinant nucleophosmin, followed by peroxidase-conjugated protein A and developed with ECL. Nucleophosmin could be detected in the nuclear extracts. Thus, nucleophosmin could be coprecipitated using antibodies against protein H demonstrating an in vivo interaction between nucleophosmin and protein H.

Figure 4:
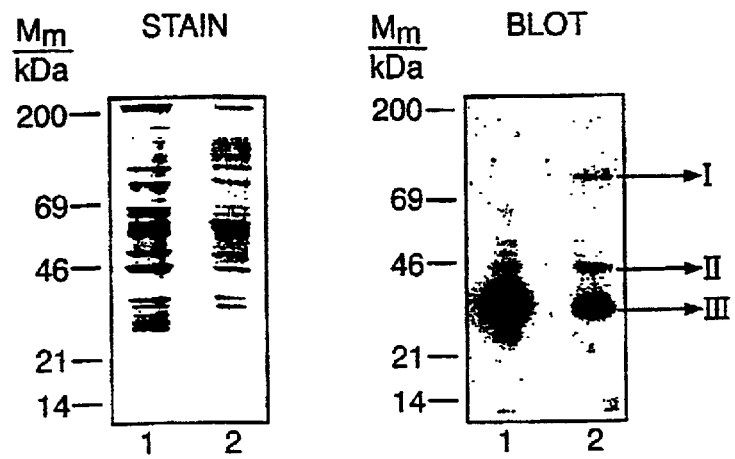
FIG. 4. Identification of nuclear proteins interacting with protein H (SEQ ID NOS: 12–19). SDS-PAGE gels identifying NPM, protein SET and hnRNP A2/B1.

Identification of Nuclear Proteins Interacting with Protein H p Unlike the homogeneous nuclear staining seen with protein H, anti-NPM antibodies detect a granular accumulation of NPM in nucleoli (Borer et al., 1989). To investigate whether protein H after the entry into the nucleus, presumably together with NPM, interacts with nuclear proteins, nuclear extracts from Jurkat cells were run on protein H-Sepharose. Several bands were eluted (see FIG. 4, STAIN, lane 2) but when probed with radiolabelled protein H, only three reacted with the probe (FIG. 4, BLOT, lane 2). These bands have apparent molecular masses of 39, 42 and 80 kDa, respectively. The 39 and 80 kDa bands (I and III, respectively) were identified as the SET protein by microsequencing. This protein was initially described as an oncogene product fused to a protein called CAN (v. Lindern et al., 1992). Three tryptic fragments each of the 39 and 80 kDa bands were subjected to $NH_2$-terminal sequencing and all sequences were related to the SET protein (FIG. 4, lower section). This fact and the molecular mass of the 80 kDa band, suggest that it represents a SET dimer. The amino acid sequence of the 42 kDa band (band II, FIG. 4) identified this band to be heterogeneous nuclear ribonuclear protein (hnRNP) A2/B1, a member of the hnRNP family (Dreyfuss et al., 1993).

Figure 5:
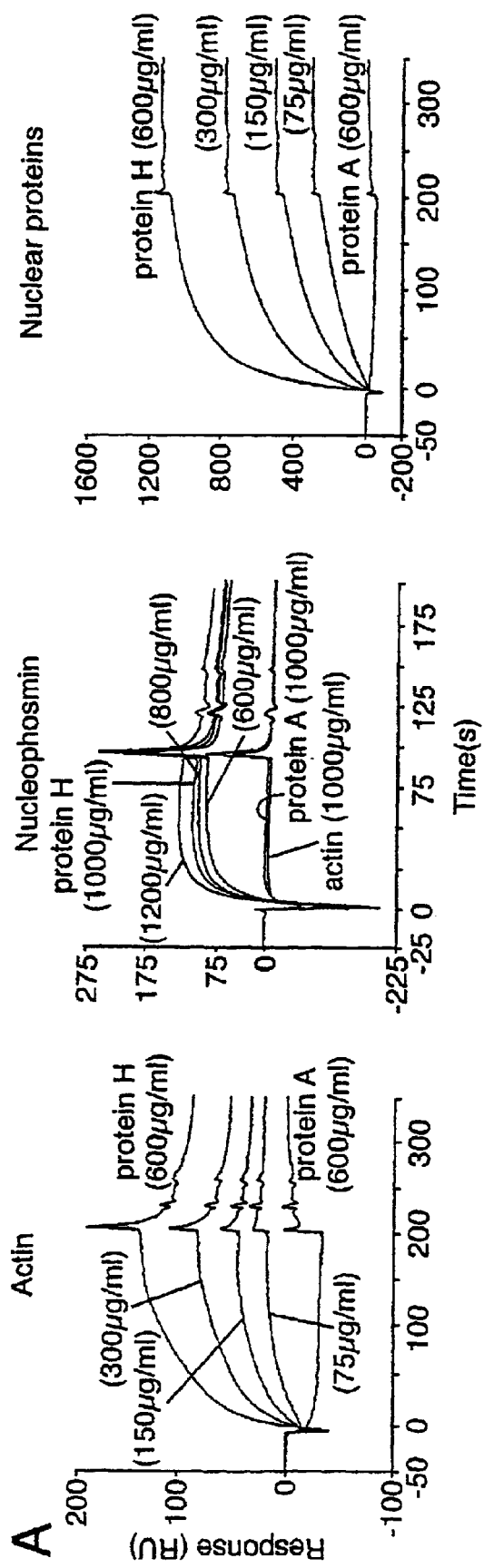
FIG. 5. Analysis of the binding of protein H to nucleophosmin and nuclear proteins. (A) Overlay plots of binding of proteins A and H to immobilised NPM (left) or nuclear proteins (right) using plasmon resonance spectroscopy. (B) Competitive inhibition of the binding of $^{125}$I-labelled NPM to protein H-Sepharose with different amounts of unlabeled NPM.
Figure 5:
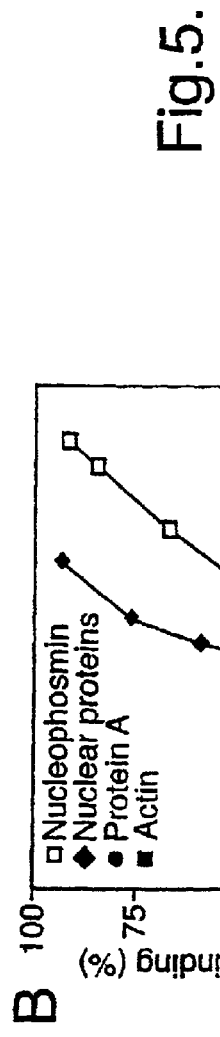

Further Analyses and Comparison between the Interactions of Protein H with Actin, NPM and the Nuclear Proteins To analyse the interactions between protein H and the various intracellular proteins in more detail, plasmon resonance spectroscopy was utilized. In these experiments different amounts of protein H were applied and left to interact with immobilized actin, NPM or with immobilized protein H-binding nuclear proteins, to the level of saturation (FIG. 5A). The NPM used in these experiments corresponds to the material shown in FIG. 3C, and to create an experimental situation similar to in vivo conditions, a mixture of the nuclear proteins interacting with protein H was used for both plasmon spectroscopy and competitive binding experiments (see FIG. 4, STAIN, lane 2).

FIG. 5A shows typical sensorgrams for the interactions between protein H-actin, protein H-NPM and protein H-nuclear proteins. On the basis of these experiments, dissociation and association rates were calculated, and used to determine association and dissociation constants (FIG. 5B). The data demonstrate that protein H has high affinity for actin but also readily dissociates from the complex, and that protein H has a higher association rate and a considerably slower dissociation rate for the nuclear proteins as compared to NPM. Also, competitive binding experiments in which NPM and the nuclear proteins simultaneously compete for the binding of protein H, showed that unlabeled nuclear proteins more efficiently inhibited the interaction between radiolabelled NPM and protein H-Sepharose, than unlabeled NPM itself. In contrast, actin did not interfere with NPM-protein H binding (FIG. 5C) and neither did actin interact with immobilized NPM (FIG. 5A, middle section). In none of these experiments did staphylococcal protein A show affinity for actin, NPM or the nuclear proteins (FIGS. 5A and C). In summary, the data on the binding kinetics provide an explanation for the release of protein H from its complex with NPM, and its nuclear accumulation as a result of the binding to the nuclear proteins SET and hnRNP A2/B1.

Soluble Protein H has a Cytostatic Effect on Murine B Cells

Figure 6:
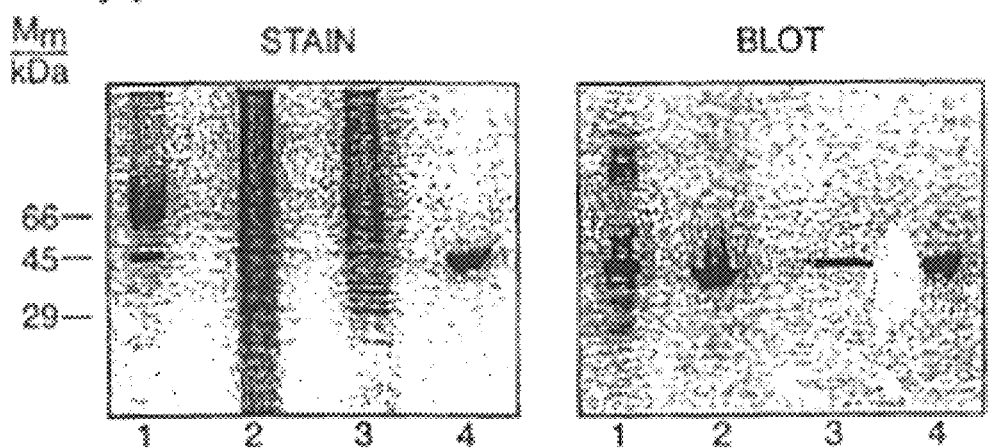
FIG. 6. Nuclear uptake and cytostatic effect of protein H. (A) SDS-PAGE gels of purified murine B cells incubated with LPS and protein H for 24 hours stained with Coomassie (left) or blotted to a PVDF membrane (right), with the blotted membrane probed with an anti-protein H antiserum, followed by peroxidase-conjugated protein A and developed with ECL. (B) Inhibition of proliferation of murine splenic B cells in response to proteins H and A.
Figure 6:
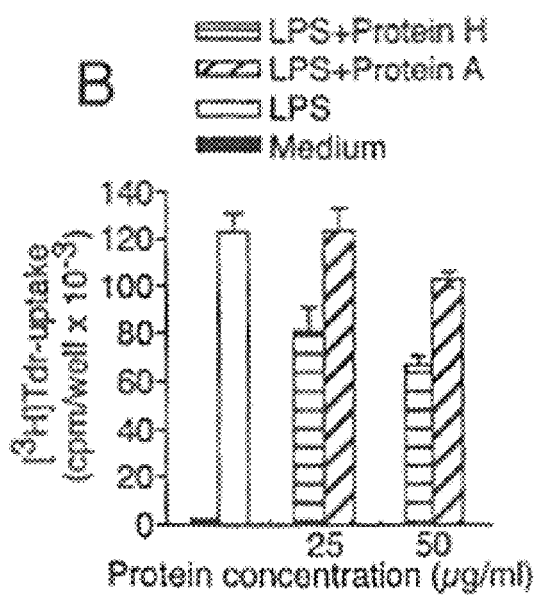

The interaction with the SET protein, a putative transcription factor and oncogene product, and hnRNP A2/B1, a molecule participating in mRNA processing, suggested that protein H could interfere with various cell functions and that metabolically active cells could be particularly sensitive to protein H. It has been shown that protein H interacts also with murine lymphocytes (Axcrona et al., 1995), and the effect of protein H on the proliferation of these cells was therefore investigated. Initially we investigated whether protein H when added to LPS-stimulated murine B cells, was transported to the nucleus, and Western blot experiments demonstrated that this was the case (FIG. 6A). There is no indication that protein H is degraded on its way from the exterior of the cell into the nucleus. Thus, the molecular mass of protein H identified in the medium, the cytoplasm and the nucleus is very similar if not identical. As a control, an identical PVDF membrane as in FIG. 6A was incubated with pre-immune serum followed by peroxidase-conjugated protein A. No signals were obtained. Following 24 hours of incubation with protein H, the cytoplasm contained 1.4, and the nuclei 2.4 ng of protein H per $10^6$ B cells. Moreover, addition of protein H to the LPS-stimulated B cells, inhibited proliferation measured as [$^3$H]Tdr-uptake in a dose dependent manner (FIG. 6B). A 50 percent inhibition was recorded at the highest protein H concentration tested. (50 µg/ml). As determined by morphology and DNA laddering, protein H did not induce apoptosis in the LPS-stimulated B cells.

Legends to Figures

FIG. 1.

Binding of protein H to the surface of human peripheral blood lymphocytes and the human Jurkat T cell line determined by FACS analysis.

(A) Staining of T cells with CD3, CD4, and CD8 versus protein H. Granulocytes were gated out with side scatter/forward scatter and stained with protein H. (B) Jurkat T cells were stained with protein H and CD45. Background staining is shown with FITC avidin and CD3 on the granulocyte gated cells and with g1-FITC/g2-PE antibodies on Jurkat cells.

FIG. 2.

Uptake and nuclear accumulation of protein H in Jurkat T cells.

Jurkat T cells were incubated with biotinylated proteins H or A, cytospinned and stained with FITC coupled avidin. (A) Incubation with protein H for four hours and (B) for eight hours. (C) Incubation with protein A for eight hours.

FIG. 3.

Protein H interacts with nucleophosmin.

(A) Membrane preparations from Jurkat T cells were digested with papain and the solubilised peptides were subjected to FPLC on a Mono-Q column. Fractions (0.5 ml) eluted with a linear NaCl gradient were analysed for protein H-binding activity in a slot binding assay, and fractions 85-87 reacted with radiolabelled protein H. (B) Radiolabelled pool 85-87 material was run on protein A-Sepharose without showing affinity (left). In the right section the pooled fractions of the run-through peak from protein A-Sepharose were subjected to a protein H-Sepharose column. (C) Peak fractions of peaks I and II from protein H-Sepharose were separated by SDS-PAGE (10% gel), followed by autoradiography. Unlabeled pool 85-87 material was run in parallel. This gel was stained and bands marked by the arrows were cut out. The peptides of the bands were digested with trypsin and tryptic fragments were separated by HPLC. $NH_2$-terminal sequences could be determined from one HPLC peak each of the two bands. These sequences (SEQ ID Nos. 9, 10, and 11) established that both bands contained NPM. Numbers indicate amino acid residue positions in the NPM sequences. (D) In vitro translated and $^{35}$S-methionine-labelled NPM peptides were separated by SDS-PAGE (13.6% gel). The gel was dried and subjected to autoradiography (left). Lane number corresponds to the peptide run and the peptides are shown schematically in the lower part of the figure. In the COOH-terminal peptide 3, X indicates putative nuclear localization signals. The three radiolabelled peptides were separately applied to protein H-Sepharose. Following extensive washing, bound material was eluted with 3M KSCN, dialyzed against PBS, concentrated and run on SDS-PAGE. The gel was dried and autoradiographed (right). (E) Mapping of the NPM-binding region of protein H by competitive inhibition. The binding of $^{125}$I-labelled NPM to protein H immobilized on Sepharose was inhibited with different amounts of unlabeled intact protein H, fragments AB and A of protein H, or protein A.

FIG. 4.

Identification of nuclear proteins interacting with protein H.

A nuclear extract was prepared from Jurkat T cells (lane 1). The extract was precleared with glycine-Sepharose followed by incubation with protein H-Sepharose. After extensive washing proteins bound to the protein H-Sepharose were eluted with 3 M KSCN, dialyzed against PBS and separated by SDS-PAGE (lane 2). Two identical gels (10%) were run simultaneously; one was stained with Coomassie blue (STAIN), one was blotted onto a PVDF membrane and probed with $^{125}$I -labelled protein H (BLOT). Material corresponding to the three bands indicated was submitted to trypsin digestion, HPLC and NH$_2$-terminal sequencing. Three sequences were obtained from each of bands I (SEQ ID Nos. 12, 13, and 14) and III (SEQ ID Nos. 17, 18, and 19) showing identity to the SET protein. Band II gave rise to two sequences found in hnRNP A2/B1 (SEQ ID Nos. 15 and 16). The sequences are shown in the lower part of the figure, and numbers indicate where homologous residues in the SET and hnRNP A2/B1 are found.

FIG. 5.

Analysis of the binding of protein H to nucleophosmin and nuclear proteins.

(A) Overlay plots of the binding of proteins H and A to immobilized actin (left), NPM (middle) or nuclear proteins (right) using plasmon resonance spectroscopy. Increasing concentrations of protein H were applied for 3 min. each during association phase. Dissociation of bound proteins was measured (expressed in resonance units, RU) following injection of buffer alone.

Affinity rates and dissociation constants for the interactions between protein H and actin, immobilized NPM or nuclear proteins are as follows (values are mean±standard deviation from three experiments).

| | Actin-Protein H | NPM-Protein H | Nuclear proteins-Protein |
|---|---|---|---|
| Association rate ($10^3 \times s^{-1}M^{-1}$) | 2.5 ± 0.1 | 6.7 ± 0.82 | 1.7 ± 0.5 |
| Dissociation rate ($10^5 \times s^{-1}$) | 150 ± 6.6 | 190 ± 2.9 | 6.7 ± 0.6 |
| Association constant ($10^6 \times M^{-1}$) | 1.7 ± 0.2 | 3.6 ± 0.5 | 26.2 ± 9.2 |
| Dissociation constant ($10^{-8} \times M$) | 60.0 ± 5.7 | 28.6 ± 3.7 | 4.4 ± 1.7 |

(B) Competitive inhibition of the binding of $^{125}$I-labelled NPM to protein H-Sepharose with different amounts of unlabeled NPM, nuclear proteins, protein A or actin.

FIG. 6.

Nuclear uptake and cytostatic effect of protein H.

(A) 7×10$^7$ purified murine B cells were incubated with LPS and protein H for 24 hours. Medium (1), cytoplasmic material (2), nuclear extract (3), and protein H (4) were run on SDS-PAGE and stained with Coomassie (left) or blotted to a PVDF membrane (right). The blotted membrane was probed with an anti-protein H antiserum, followed by peroxidase-conjugated protein A and developed with ECL. (B) Inhibition of proliferation of murine splenic B cells in response to proteins H and A.

```
Sequence Information
Given below are the CDNA (SEQ ID No.5) and amino acid
(SEQ ID No.6) sequences of protein H. The boundaries of
the S, A, C1, C2, C3 and D regions are marked, as are the
N-termini of the alternative forms of protein H.

ATG ACT AGA CAA CAA ACC AAG AAA
                            Met Thr Arg Gln Gln Thr Lys Lys
                            -41
                            Signal peptide (Region S)

AAT TAT TCA CTA CGG AAA CTA AAA ACC GGT ACG GCT TCA GTA GCC GTT
Asn Tyr Ser Leu Arg Lys Leu Lys Thr Gly Thr Ala Ser Val Ala Val

GCT TTG ACC GTT TTG GGC GCA GGT TTT GCA AAC CAA ACA ACA GTT AAG
Ala Leu Thr Val Leu Gly Ala Gly Phe Ala Asn Gln Thr Thr Val Lys

GCG|GAA GGG GCT AAA ATT GAT TGG CAA GAA GAG TAT AAA AAG TTA GAC
Ala|Glu Gly Ala Lys Ile Asp Trp Gln Glu Glu Tyr Lys Lys Leu Asp
 -1 |1
     Mature protein, Region A GAA GAT AAT GCT AAA CTT GTT GAG GTT GTT GAA ACC ACA AGT TTG GAA
Glu Asp Asn Ala Lys Leu Val Glu Val Val Glu Thr Thr Ser Leu Glu
```

-continued

```
AAC GAA AAA CTC AAG AGT GAG AAT GAG GAG AAT AAG AAA AAT TTA GAC
Asn Glu Lys Leu Lys Ser Glu Asn Glu Glu Asn Lys Lys Asn Leu Asp

AAA CTT AGC AAA GAA AAT CAA GGA AAG CTC GAA AAA TTG GAG CTT GAC
Lys Leu Ser Lys Glu Asn Gln Gly Lys Leu Glu Lys Leu Glu Leu Asp

TAT CTC AAA AAA TTA GAT CAC GAG CAC AAA GAG CAC CAA AAA GAA CAA
Tyr Leu Lys Lys Leu Asp His Glu His Lys Glu His Gln Lys Glu Gln

CAA|GAA CAA GAA GAG CGA CAA AAA AAT CAA GAA CAA TTA GAA CGT AAA
Gln|Glu Gln Glu Glu Arg Gln Lys Asn Gln Glu Gln Leu Glu Arg Lys
 80 |81
     Region B TAC CAA CGA GAA GTA GAA AAA CGT TAT CAA GAA CAA CTC CAA AAA CAA
Tyr Gln Arg Glu Val Glu Lys Arg Tyr Gln Glu Gln Leu Gln Lys Gln CAA CAA TTA GAA ACA GAA|AAG CAA ATC TCA GAA GCT AGT CGT AAG AGC
Gln Gln Leu Glu Thr Glu|Lys Gln Ile Ser Glu Ala Ser Arg Lys Ser
                    117|118
                        Region C1

CTA AGC CGT GAC CTT GAA GCG TCT CGT GCA GCT AAA AAA GAC CTT GAA
Leu Ser Arg Asp Leu Glu Ala Ser Arg Ala Ala Lys Lys Asp Leu Glu

GCT GAG CAC CAA AAA CTT GAA GCT GAG CAC CAA AAA CTT AAA GAA|GAC
Ala Glu His Gln Lys Leu Glu Ala Glu His Gln Lys Leu Lys Glu|Asp
                                                      158|159
                                                         Region C2

AAA CAA ATC TCA GAC GCA AGT CGT CAA GGC CTA AGC CGT GAC CTT GAA
Lys Gln Ile Ser Asp Ala Ser Arg Gln Gly Leu Ser Arg Asp Leu Glu

GCG TCT CGT GCA GCT AAA AAA GAG CTT GAA GCA AAT CAC CAA AAA CTT
Ala Ser Arg Ala Ala Lys Lys Glu Leu Glu Ala Asn His Gln Lys Leu

GAA GCT GAG CAC CAA AAA CTT AAA GAA|GAC AAA CAA ATC TCA GAC GCA
Glu Ala Glu His Gln Lys Leu Lys Glu|Asp Lys Gln Ile Ser Asp Ala
                                200|201
                                   Region C3

AGT CGT CAA GGC CTA AGC CGT GAC CTT GAA GCG TCT CGT GCA GCT AAA
Ser Arg Gln Gly Leu Ser Arg Asp Leu Glu Ala Ser Arg Ala Ala Lys

AAA GAG CTT GAA GCA AAT CAC CAA AAA CTT GAA GCA GAA GCA AAA GCA
Lys Glu Leu Glu Ala Asn His Gln Lys Leu Glu Ala Glu Ala Lys Ala

CTC AAA GAA|CAA TTA GCG AAA CAA GCT GAA GAA CTT GCA AAA CTA AGA
Leu Lys Glu|Gln Leu Ala Lys Gln Ala Glu Glu Leu Ala Lys Leu Arg
        242|243
            Region D GCT GGA AAA GCA TCA GAC TCA CAA ACC CCT GAT ACA AAA CCA GGA AAC
Ala Gly Lys Ala Ser Asp Ser Gln Thr Pro Asp Thr Lys Pro Gly Asn AAA GCT GTT CCA GGT AAA GGT CAA GCA CCA CAA GCA GGT ACA|AAA CCT
Lys Ala Val Pro Gly Lys Gly Gln Ala Pro Gln Ala Gly Thr|Lys Pro
                                                    285|286
Approx C-terminus of protein H cleaved from S. pyogenes|

AAC CAA AAC AAA GCA CCA ATG AAG GAA ACT AAG AGA CAG TTA CCA TCA
Asn Gln Asn Lys Ala Pro Met Lys Glu Thr Lys Arg Gln Leu Pro Ser
                                C-terminus of protein H produced in ACA GGT|GAA ACA GCT AAC CCA TTC TTC ACA GCG GCA GCC CTT ACT GTT
Thr Gly|Glu Thr Ala Asn Pro Phe Phe Thr Ala Ala Ala Leu Thr Val
    305|306
E. Coli|

ATG GCA ACA GCT GGA GTA GCA GCA GTT GTA AAA CGC AAA GAA GAA AAC
Met Ala Thr Ala Gly Val Ala Ala Val Val Lys Arg Lys Glu Glu Asn
                                                            335
                C-terminus of full, mature protein H
```

References

Åkerström, B., and Björck, L. (1989). Protein L: an immunoglobulin light chain-binding bacterial protein. Characterization of binding and physicochemical properties. J. Biol. Chem. 264, 19740–19746.

Åkesson, P., Cooney, J., Kishimoto, F., and Björck, L. (1990). Protein H—a novel IgG binding bacterial protein. Mol. Immunol. 27, 523–531.

Åkesson, P., Schmidt, K.-H., Cooney, J., and Björck, L. (1994). M1 protein and protein H: IgGFc and albumin-binding streptococcal surface proteins encoded by adjacent genes. Biochem. J. 300, 877–886.

Altschul, S. F., Gish, W., Miller, W., Myers, E. W., and Lipman, D. J. (1990). Basic local alignment search tool. J. Mol. Biol. 215, 403–410.

Axcrona, K., Björck, L., and Leanderson, T. (1995). Multiple ligand interactions for bacterial immunoglobulin-binding proteins on human and murine cells of the hematopoetic lineage. Scand. J. Immunol. 42, 359–367.

Berge, A., and Björck, L. (1995). Streptococcal cysteine proteinase releases biologically active fragments of streptococcal surface proteins. J. Biol. Chem. 270, 9862–9867.

Borer, R. A., Lehner, C. F., Eppenberger, H. M., and Nigg, E. A. (1989). Major nucleolar proteins shuttle between nucleus and cytoplasm. Cell 56, 379–390.

Dreyfuss, G., Matunis, M. J., Pinol-Roma, S., and Burd, C. G. (1993). hnRNP proteins and the biogenesis of mRNA. Ann. Rev. Biochem. 62, 289–321.

Frick, I.-M., Åkesson, P., Cooney, J., Sjöbring, U., Schmidt, K.-H., Gomi, H., Hattori, S., Tagawa, C., Kishimoto, F., and Björck, L. (1994). Protein H—a surface protein of *Streptococcus pyogenes* with separate binding sites for IgG and albumin. Mol. Microbiol. 12, 143–151.

Frick, I.-M., Crossin, K. L., Edelman, G. M., and Björck, L. (1995). Protein H- a bacterial surface protein with affinity for both immunoglobulin and fibronectin type III domains. EMBO J. 14, 1674–1679.

Herrera, J. E., Correia, J. J., Jones, A. E., and Olson, M. O. J. (1996). Sedimentation analyses of the salt- and divalent metal ion-induced oligomerization of nucleolar protein B23. Biochemistry 35, 2668–2673.

Herrmann, C., Volknandt, W., Wittich, B., Kellner, R., and Zimmermann, H. (1996). The major vault protein (MVP100) is contained in cholinergic nerve terminals of electric ray electric organ. J. Biol. Chem. 271, 13908–13915.

Herwald, H., Collin, M., Müller-Esterl, W., and Björck, L. (1996). Streptococcal cysteine proteinase releases kinins: a novel virulence mechanism. J. Exp. Med. 184, 665–673.

Herwald, H., Dedio, J., Kellner, R., Loos, M., and Müller-Esterl, W. (1996). Isolation and characterization of the kininogen-binding protein p33 from endothelial cells. Identity with the gC1q receptor. J. Biol. Chem. 271, 13040–13047.

Holm, S. E., Norrby, A., Bergholm, A. M., and Norgren, M. (1992). Aspects of pathogenesis of serious group A streptococcal infections in Sweden, 1988–1989. J. Infect. Dis. 166, 31–37.

Mirkovitch, J., Mirault, M. E., and Laemmli, U. K. (1984). Organization of the higher-order chromatin loop: specific DNA attachment sites on nuclear scaffold. Cell 39, 223–232.

Schmidt-Zachmann, M., HŸgle-Dörr, B., and Franke, W. W. (1987). A constitutive nucleolar protein identified as a member of the nucleoplasmin family. EMBO J. 6, 1881–1890.

Umekawa, H., Chang, J.-H., Correia, J. J., Wang, D., Wingfield, P. T., and Olson, M. O. J. (1993). Nucleolar protein B23: bacterial expression, purification, oligomerization and secondary structures of two isoforms. Cell. Mol. Biol. Res. 39, 635–645.

v. Lindern, M., v. Baal, S., Wiegant, J., Raap, A., Hagemeijer, A., and Grosveld, G. (1992). Can, a putative oncogene associated with myeloid leukemogenesis, may be activated by fusion of its 3' half to different genes: characterization of the set gene. Mol. Cell. Biol. 12, 3346–3355.

Wang, D., Umekawa, H., and Olson, M. O. J. (1993). Expression and subcellular locations of two forms of nucleolar protein B23 in rat tissues and cells. Cell Mol. Biol. Res. 39, 33–42.

Wang, D., Baumann, A., Szebeni, A., and Olson, M. O. J. (1994). The nucleic acid binding activity of nucleolar protein B23.1 resides in its carboxyl-terminal end. J. Biol. Chem. 269, 30994–30998.

---

What is claimed is:

1. A method of exerting a cytostatic effect on a eukaryotic cell comprising administering to said cell an effective non-toxic amount of protein H of S. pyogenes or a fragment comprising the A region of protein H of S. pyogenes which is capable of exerting a cytostatic effect on said eukaryotic cell wherein the cell comprises a tumour cell, a virus infected cell or a proliferating cell, and wherein said cell is a lymphocyte.

2. A method of combating undesired cell proliferation comprising administering to a eukaryotic cell an effective non-toxic amount of protein H of S. pyogenes or a fragment comprising the A region of protein H which is capable of exerting a cytostatic effect on said eukaryotic cell, wherein said cell is a lymphocyte.

3. A method for the treatment of cancerous lymphocytes, virally infected lymphocytes, or for treating an inflammatory condition associated with proliferation of lymphocytes, said method comprising administering to the lymphocytes an effective non-toxic amount of protein H of S. pyogenes or a fragment comprising the A region of protein H of S. pyogenes.

4. A method according to claim 1 wherein said lymphocyte is expressing nucleophosmin (NPM)/B23 before the administration of protein H of S. pyogenes or the fragment comprising the A region of protein H of S. pyogenes.

5. A method according to claim 1, wherein a fragment comprising the A region of protein H is administered to the lymphocyte.

6. A method according to claim 1, wherein the fragment of protein H further comprises the AB region of protein H.

* * * * *